(12) United States Patent
Mir

(10) Patent No.: US 10,351,490 B2
(45) Date of Patent: *Jul. 16, 2019

(54) COMPLEXES OF 1-METHYLCYCLOPROPENE WITH METAL COORDINATION POLYMER NETWORKS

(71) Applicant: AGROFRESH INC., Collegeville, PA (US)

(72) Inventor: Nazir Mir, Somerset, NJ (US)

(73) Assignee: AGROFRESH INC., Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/673,054

(22) Filed: Aug. 9, 2017

(65) Prior Publication Data
US 2017/0369401 A1 Dec. 28, 2017

Related U.S. Application Data

(63) Continuation of application No. 15/206,707, filed on Jul. 11, 2016, which is a continuation of application No. 14/726,004, filed on May 29, 2015, now Pat. No. 9,394,216.

(60) Provisional application No. 62/077,867, filed on Nov. 10, 2014.

(51) Int. Cl.

| | | |
|---|---|---|
| A01N 25/10 | (2006.01) | |
| A01N 27/00 | (2006.01) | |
| C07F 7/10 | (2006.01) | |
| C07F 15/02 | (2006.01) | |
| C07F 15/06 | (2006.01) | |
| C07F 1/08 | (2006.01) | |
| C07D 251/12 | (2006.01) | |
| C07C 55/02 | (2006.01) | |
| C07C 53/06 | (2006.01) | |
| C07C 7/12 | (2006.01) | |
| C07C 317/44 | (2006.01) | |
| C07C 7/10 | (2006.01) | |
| C07C 317/14 | (2006.01) | |
| C07F 3/02 | (2006.01) | |
| C07F 3/06 | (2006.01) | |
| B01J 20/22 | (2006.01) | |
| A01N 3/00 | (2006.01) | |

(52) U.S. Cl.
CPC ............... C07C 7/12 (2013.01); A01N 3/00 (2013.01); A01N 25/10 (2013.01); A01N 27/00 (2013.01); B01J 20/226 (2013.01); C07C 7/10 (2013.01); C07C 53/06 (2013.01); C07C 55/02 (2013.01); C07C 317/14 (2013.01); C07C 317/44 (2013.01); C07D 251/12 (2013.01); C07F 1/08 (2013.01); C07F 3/02 (2013.01); C07F 3/06 (2013.01); C07F 15/02 (2013.01); C07F 15/06 (2013.01)

(58) Field of Classification Search
CPC ................................. C07C 7/10; A01N 25/10
USPC ....................................... 504/357, 359, 354
See application file for complete search history.

(56) References Cited

U.S. PATENT DOCUMENTS

| | | |
|---|---|---|
| 5,518,988 A | 5/1996 | Sisler et al. |
| 6,017,849 A | 1/2000 | Daly et al. |
| 6,194,350 B1 | 2/2001 | Sisler |
| 6,313,068 B1 | 11/2001 | Daly et al. |
| 6,365,549 B2 | 4/2002 | Sisler |
| 6,426,319 B1 | 7/2002 | Kostansek |
| 6,444,619 B1 | 9/2002 | Kostansek |
| 6,548,448 B2 | 4/2003 | Kostansek |
| 6,762,153 B2 | 7/2004 | Kostansek et al. |
| 6,770,600 B1 | 8/2004 | Lamola et al. |
| 6,897,185 B1 | 5/2005 | Chang et al. |
| 6,953,540 B2 | 10/2005 | Chong et al. |
| 8,093,430 B2 | 1/2012 | Sisler |
| 8,163,244 B2 | 4/2012 | Yoo |
| 8,314,051 B2 | 11/2012 | Yoo |
| 8,343,261 B2 | 1/2013 | Leung et al. |
| 8,431,744 B2 | 4/2013 | Leung et al. |
| 8,461,086 B2 | 6/2013 | Chang et al. |
| 8,541,344 B2 | 9/2013 | Kostansek et al. |
| 8,552,189 B2 | 10/2013 | Park et al. |
| 8,569,407 B2 | 10/2013 | Leung |
| 8,603,524 B2 | 12/2013 | Baier et al. |
| 8,802,140 B2 | 8/2014 | Mir |
| 8,822,382 B2 | 9/2014 | Mir |

(Continued)

FOREIGN PATENT DOCUMENTS

| | | |
|---|---|---|
| CN | 100340172 C | 10/2007 |
| CN | 101297659 A | 11/2008 |

(Continued)

OTHER PUBLICATIONS

Petition for Inter Partes Review of U.S. Pat. No. 9,394,216, filed Aug. 8, 2017, 79 pages.

(Continued)

*Primary Examiner* — Venkataraman Balasubramanian
(74) *Attorney, Agent, or Firm* — Barnes & Thornburg LLP

(57) ABSTRACT

Disclosed are adsorption complexes that include 1-methylcyclopropene (1-MCP) and a metal coordination polymer network (MCPN), wherein the MCPN is a porous material, and the 1-MCP is adsorbed into the MCPN. Also disclosed are kits for containing 1-MCP that include the adsorption complex in a 1-MCP-impermeable package. Also disclosed are methods of releasing 1-methylcyclopropene (1-MCP) from the kit that include the application of aqueous fluids, heat, and/or pressure.

19 Claims, 10 Drawing Sheets

(56) References Cited

U.S. PATENT DOCUMENTS

| | | | |
|---|---|---|---|
| 9,394,216 B2* | 7/2016 | Mir | C07C 7/10 |
| 9,908,827 B2* | 3/2018 | Mir | C07C 7/10 |
| 2003/0220201 A1 | 11/2003 | Kostansek et al. | |
| 2005/0260907 A1 | 11/2005 | Chang et al. | |
| 2005/0261132 A1 | 11/2005 | Kostansek et al. | |
| 2006/0154822 A1 | 7/2006 | Toivonen et al. | |
| 2007/0105722 A1 | 5/2007 | Basel et al. | |
| 2009/0088323 A1 | 4/2009 | Basel et al. | |
| 2010/0144533 A1 | 6/2010 | Baier et al. | |
| 2011/0034335 A1 | 2/2011 | Daly et al. | |
| 2011/0092369 A1 | 4/2011 | Chang et al. | |
| 2011/0152375 A1 | 6/2011 | Troscher et al. | |
| 2013/0074402 A1 | 3/2013 | Versteylen et al. | |
| 2013/0216657 A1 | 8/2013 | Kusuura | |
| 2013/0225413 A1 | 8/2013 | Fowler et al. | |
| 2013/0280611 A1 | 10/2013 | Alkordi et al. | |
| 2013/0345060 A1 | 12/2013 | Becker et al. | |
| 2014/0066310 A1 | 3/2014 | Edgington | |
| 2014/0080710 A1 | 3/2014 | Zhang et al. | |
| 2014/0080711 A1 | 3/2014 | Zhang et al. | |
| 2014/0080712 A1 | 3/2014 | Lao et al. | |
| 2014/0326620 A1 | 11/2014 | Mir | |
| 2014/0342910 A1 | 11/2014 | Mir | |
| 2015/0087520 A1 | 3/2015 | Ghosh | |
| 2016/0130198 A1 | 5/2016 | Mir | |
| 2017/0001929 A1 | 1/2017 | Mir | |

FOREIGN PATENT DOCUMENTS

| | | |
|---|---|---|
| CN | 101926387 A | 12/2010 |
| CN | 101971875 A | 2/2011 |
| CN | 102119719 A | 7/2011 |
| CN | 102440237 A | 5/2012 |
| CN | 102862361 A | 1/2013 |
| CN | 102964615 A | 3/2013 |
| CN | 202807462 U | 3/2013 |
| CN | 102167706 | 12/2014 |
| EP | 1 192 858 | 4/2002 |
| EP | 1 593 306 | 11/2005 |
| EP | 2100661 A2 | 9/2009 |
| EP | 2296171 A2 | 3/2011 |
| TW | 1445500 B | 7/2014 |
| WO | WO 2006/072180 | 7/2006 |
| WO | WO 2008/089140 | 7/2008 |
| WO | WO 2014056035 A1 | 4/2014 |
| WO | WO 2014/172900 | 10/2014 |
| WO | WO2016/037043 | 3/2016 |

OTHER PUBLICATIONS

Declaration of Mircea Dinca, Ph.D., dated Aug. 7, 2017, submitted as an Exhibit in the Inter Partes Review of U.S. Pat. No. 9,394,216, filed Aug. 8, 2017, 126 pages.
Lan, A. et al., "A Luminescent Microporous Metal-Organic Framework for the Fast and Reversible Detection of High Explosives," Angew. Chem. Int. Ed., 2009, 48, 2334-2338.
Lee, Y. et al., "Development of a 1-Methylcyclopropene (1-MCP) Sachet Release System," Journal of Food Science, 2006, 71, 6 pages.
Ho, T. et al., "Encapsulation of gases in powder solid matrices and their applications: A review," Powder Technology, 2014, 259, 87-108.
Horcajada, P. et al., "Metal-Organic Frameworks in Biomedicine," Chem. Rev., 2012, 112, 1232-1268.
Rood, J. et al., "Synthesis, Structural Characterization, Gas Sorption and Guest-Exchange Studies of the Lightweight, Porous Metal-Organic Framework a-[Mg3(O2CH)6]," Inorganic Chemistry, 2006, 45, 5521-5528.
Burtch, N. et al., "Water Stability and Adsorption in Metal-Organic Frameworks," Chem. Rev., 2014, 114, 10575-10612.
Bloch, E. et al., "Hydrocarbon Separations in Metal-Organic Framework with Open Iron(II) Coordination Sites," Science, 2012, 335, 1606-1610.
Hartmann, M. et al., "Adsorptive Separation of Isobutene and Isobutane on Cu3(BTC)2," Langmuir, 2008, 24, 8634-8642.
Blankenship, S. et al., "1-Methylcyclopropene: a review," Postharvest Biology and Technology, 2003, 28, 1-25.
Cozmuta, I. et al., "Gas sorption and Barrier Properties of Polymeric Membranes from Molecular Dynamics and Monte Carlo Simulations," J. Phys. Chem., 2007, 111, 3151-3166.
Declaration of Yieyie Yang, Ph.D., dated Aug. 8, 2017, submitted as an Exhibit in the Inter Partes Review of U.S. Pat. No. 9,394,216, filed Aug. 8, 2017, 8 pages.
U.S. Appl. No. 62/046,667, filed Sep. 5, 2014, 62 pages.
Partial Supplementary European Search Report for EPC Application No. 14794851.7, dated Nov. 23, 2016, 7 pages.
Alvarez et al., "The Structure of the Aluminum Fumarate Metal-Organic Framework A520," Anqew. Chem., 127, 3735-3739, 2015.
Banerjee et al., "A Calcium Coordination Framework Having Permanent Porosity and High CO2/N2 Selectivity," *Crystal Growth Des.*, 12, 2162-2165, 2012.
Breslow et al., "Very Strong Binding of Appropriate Substrates by Cyclodextrin Dimers," *J. Am. Chem. Soc.*, 111, 8296-8297, 1989.
Chen et al., "A two-dimensional zeolitic imidazolate framework with a cushion-shaped cavity for CO2 adsorption," *Chem. Commun.*, 49, 9500-9502, 2013.
Dinca et al., Strong H2 Binding and Selective Gas Adsorption within the Microporous Coordination Solid Mg3(O2C-C10H5-CO2)3, *J. Am. Chem. Soc.*,127, 9376-9377, 2005.
International Search Report and Written Opinion issued in related PCT Application No. PCT/US2015/059680 dated Feb. 2, 2016, 8 pages.
Kopel et al., "Complexes of iron(III) salen and saloph Schiff bases with bridging dicarboxylic and tricarboxylic acids," *Transition Met. Chem.*, 23, 139-142, 1998.
Krungleviciute et al., "Argon Adsorption on Cu3(Benzene-1,3,5-tncarboxylatejal+O)s Metal—Organic Framework," *Langmuir*, 23, 3106-3109, 2007.
Lan et al., "RPM3: A Multifunctional Microporous MOF with Recyclable Framework and High H2 Binding Energy," *Inorg. Chem.*, 48, 7165-7173, 2009.
Loiseau et al., "A Rationale for the Large Breathing of the Porous Aluminum Terephthalate (MIL-53) Upon Hydration," *Chem. Eur. J.*, 10, 1373-1382, 2004.
Mir et al., "Harvest Maturity, Storage Temperature, and 1-MCP Application Frequency Alter Firmness Retention and Chlorophyll Fluorescence of 'Redchief Delicious' Apples," *J. Amer. Soc. Hort. Sci*, 126(5):618-624, 2001.
Neoh et al., "Kinetics of Molecular Encapsulation of 1-Methylcyclopropene into a-Cyclodextrin," *J. Aotic. Food Chem.*, 55, 11020-11026, 2007.
Pan et al., "RPM-1: A Recyclable Nanoporous Material Suitable for Ship-In-Bottle Synthesis and Large Hydrocarbon Sorption," *Angew. Chem. Int. Ed.*,42, No. 5, 2003.
Pan et al., "RPM-2: A recyclable porous material with unusual adsorption capability: self assembly via structural transformations," *Chem. Commun.*, 854-855, 2003.
Qian et al., "Hydrothermal synthesis of zeolitic imidazolate framework-67 (ZIF-67) nanocrystals," *Materials Letters*, 82, 220-223, 2012.
Rossin et al., "Phase Transitions and CO2 Adsorption Properties of Polymeric Magnesium Formate," *Growth & Design*, vol. 8, No. 9, 3302-3308, 2008.
Wang et al., "Stability and hydrogen absorption of metal-organic frameworks prepared via different catalyst doping methods," Journal of Catalysis, 318, 128-142, 2014.
Defendants' Opening Claim Construction Brief, *UPL Ltd. v. AgroFresh Inc.*, AgroFresh Exhibit 2052, IPR2017-01919.
Defendants' Responsive Claim Construction Brief, *UPL Ltd. v. AgroFresh Inc.*, AgroFresh Exhibit 2053, IPR2017-01919.
Deposition of Krista S. Walton, Ph.D., *UPL Ltd. v. AgroFresh Inc.*, UP Exhibit 1054, IPR2017-01919.
Getman, R. et al., "Review and Analysis of Molecular simulations of Methane, Hydrogen, and Acetylene Storage in Metal-Organic Frameworks," Chemical Reviews, 2012, 112, 703-723.

(56) References Cited

OTHER PUBLICATIONS

Maji et al., "A flexible interpenetrating coordination framework with a bimodal porous functionality," Nature Materials, vol. 6, Feb. 2007, 142-148.
Patent Owner Sur-Reply, Oct. 9, 2018, IPR2017-01919.
Petitioner's Reply to Patent Owner's Response to Petition, Sep. 10, 2018, IPR2017-01919.
Tour et al., "IV.C.1f Nanoengineering the Forces of Attraction in a metal-Carbon Array for H2 Uptake at Room Temperature," DOE Hydrogen Program, FY 2008 Annual Progress Report, 640-643.
*UPL Ltd.* v. *AgroFresh Inc.*, UPL Exhibit 1047, IPR2017-01919.
Jun. 27, 2016 email from Robert (Lynn) Oakes to Francois Girin titled "EPA Inerts Group Approval Letter" with EPA approval letter attached.
Jul. 11, 2016 Decco/ESSENTIV announcement of EPA registration of TruPick.
"Absorbents: Fundamentals and Applications," Chapter 3, edited by Ralph T. Yang, John Wiley & Sons, Inc., 2003.(45 pages).
Ahmad et al., "Elemental distribution and porosity enhancement in advanced nano bimetallic catalyst," Powder Technology 280 (2015), 42-52.
Ambaw et al., "Modeling the diffusion-adsorption kinetics of 1-methylcyclopropene (1-MCP) in apple fruit and non-target materials in storage rooms," Journal of Food Engineering, vol. 102, No. 3, Feb. 2011, pp. 257-265.
Appel et la., "Nonideal Adsorption Equilibria Described by Pure component Isotherms and Virial Mixture Coefficients," Ind. Eng. Chem. Res., 1998, 37, 4774-4782.
Biencinto, M. et al., "Performance model and annual yield comparison of parabolic-trough solar thermal power plants with either nitrogen or synthetic oil as heat transfer fluid," Energy Conversion and Management, 87, (2014) 238-249.S.
Calleja, G., et al., "Pure and Multicomponent Adsorption Equilibrium of Carbon Dioxide, Ethylene, and Propane on ZSM-5 Zeolites with Different Si/Al Ratios," J. Chem. Eng. Data (1998), 43, 994-1003.
"Carbon Nanotube Research," ScienceDirect Search Alert, Apr. 4, 2018 http://carbonnanotuberesearch.blogspot.com/2014/03/sciencedirect-search-alert-carbon_29 . . . .
Chopra, S. et al., "Metal-organic frameworks have utility in adsorption and release of ethylene and 1-methylcyclopropene in fresh produce packaging," Postharvest Biology and Technology 130 (2017) 48-55.
Das, D., et al., "Various types of separation membranes," Current Science, vol. 110, No. 8, Apr. 25, 2016, 1426-1438.
Decision, Institution of Inter Partes Review, Case IPR2017-01919, Mar. 7, 2018.
Declaration of Dr. Ann Beaulieu, Case No. IPR2017-01919, Ex. No. 2045, Jun. 6, 2018.
Declaration of Joshua P. Larsen, Case No. IPR2017-01919, Ex. No. 2006. Dec. 13, 2017.
Declaration of Kelley Louis, J.D., M.L.I.S., Case No. IPR2017-01919, Ex. No. 2051.
Declaration of Dr. Krista S. Walton, Case No. IPR2017-01919, Ex. No. 2005, Dec. 13, 2017.
Declaration of Michael Carney, Case No. IPR2017-01919, Ex. No. 1039, Apr. 4, 2018.
Defendants Decco U.S. Post-Harvest, Inc., Cerexagri, Inc. D/B/A Decco Post-Harvest, and UPL, Ltd's Initial Invalidity Contentions, C.A. No. 16-662-JFB-SRF, Mar. 21, 2018.
Deposition of Mircea Dinca, Case No. IPR2017-01919, May 31, 2018.
Ferenczi, A. et al., "Volatile Ester Suppression and Recovery following 1-Methylcyclopropene Application to Apple Fruit," J. Amer. Soc. Hort. Sci. 131(5), 691-701, 2006.
Ho, T. et al., "Encapsulation of gases in powder solid matrices and their applications: A review," Powder Technology, vol. 259, Jun. 2014, 87-108.
Jayanty, S. et al., "Concentration Dependence of 'Redchief Delicious' Apple Fruit Softening and Chlorophyll fluorescence to Repeated Doses of 1-Methylcyclopropene," J. Amer. Soc. Hort. Sci. 129(5):760-765, 2004.
Lee, Y.S. et al., "Development of a 1-Methylcyclopropene (1-MCP) Sachet Release System," Journal of Food Science, vol. 71, No. 1, 2006, C1-C6.
Library of Congress Online Catalog, "Emerging food packaging technologies: principles and practice," edited by Kit L. Yam and Dong Sun Lee, (2002).
Mir, N.A. et al., "Harvest Maturity, Storage Temperature, and 1-MCP Application Frequency Alter Firmness Retention ad Chlorophyll Fluorescence of 'Redchief Delicious' Apples," J. Amer. Soc. Hort. Sci. 126(5), 618-624 (2001).
Mir, N. et al, Inhibiting Tomato Ripening with 1-Methylcyclopropene, J. Amer. Soc. Hort. Sci. 129(1), 112-120 (2004).
Mir, N.A. et al., "Use of 1-MCP to Reduce the Requirement for Refrigeration in the Storage of Apple Fruit," ISHS Acta Horticulturae 553: IV International Conference on Postharvest Science, https://www.actahort.org/boooks/553/553_136htm Abstract Only.
Nanthachai, N. et al., "Adsorption of 1-MCP by fresh Produce," Postharvest Biology and Technology, vol. 43, No. 3, Mar. 200, 291-297.
Neoh, T.L. et al., "Kinetics of Molecular Encapsulation of 1-Methylcyclopropene into α-Cyclodextrin," J. Agric. Food Chem. 55 (26), (2007), 11020-11026.
Padin, J. et al., "New sorbents for olefin/paraffin separations by adsorption via π-complexation: synthesis and effects of substrates," Chemical Engineering Science, 55, (2000) 2607-2616.
Pashazadeh, B. et al., 1-MCP Improved Diverse Sensorial, Biochemical and Physical Apple Ttraits During Cold Storage Based on Cultivar, Agricultural Sciences, vol. 08, No. 01 (2017), 77-96.
Patent Owner Preliminary Response, Case No. IPR2017-01919, Dec. 13, 2017.
Patent Owner Response, Case No. IPR2017-01919, Jun. 8, 2018.
Product Sheet, Shandong Aoweite Biotechnology Co., Ltd., http://www.chinesepost-harvest.com/products, 4 pages.
Rudisill, E.N. et al., "Coadsorption of Hydrocarbons and Water on BPL Activated Carbon," Ind. Eng. Chem. Res., vol. 31, No. 4, 1992, 1122-1130.
Second Supplemental Declaration of Dr. Krista S. Walton, Case No. IPR2017-01919, Exh. 2050.
Siddiq, M. et al., "Physiochemical Properties of Whole Fruit and Sensory Quality of Fresh-Cut Apples Pre-Treated with 1-Methylcyclopropene (1-MCP)," International Journal of Food Properties, 17 (2014) 1081-1092.
Supplemental Declaration of Dr. Krista S. Walton, Case No. IPR2017-01919, Exhibit No. 2049.
Supplemental Declaration of Mircea Dinca, Ph.D., Case No. IPR2017-01919, Exhibit No. 1038.
Torres-Knoop, A. et al., "Separating Xylene Isomers by Commensurate stacking of *p*-Xylene within Channels of MAF-X8**," Angew. Chem. Int. Ed. 53 (2014) 7774-7778.
Truitt, M.J. et al., "Identification of an Adsorption Complex between an Alkane and Zeolite Active Sites," J. Am. Chem. Soc., vol. 126, No. 36, 2004, 11144-11145.
Vallejo, F. et al., "Depletion of 1-MCP by 'non-target' materials from fruit storage facilities," Postharvest Biology and Technology, 40(2), May 2006, 177-182.
Wang, Y. et al., "Adsorption Equilibrium of Binary Mixtures of Carbon Dioxide and Water Vapor on Zeolites 5A and 13X," J. Chem. Eng. Data, vol. 55 (2010), 3189-3195.
Wang, Q.M. et al., "Metallo-organic molecular sieve for gas separation and purification," Microporous and Mesoporous Materials, 55 (2002) 217-230.
Yam, K.L. and Lee, D.S., ed., "Emerging food packaging technologies: Principles and practice," Case No. IPR2017-01919, Exhibit 1029.
Yang, R.T. et al., "New Sorbents for Olefin/Paraffin Separations by Adsorption via π-Complexation," AIChE Journal, vol. 41, No. 3,+2 Mar. 1995, 509-517.

(56) References Cited

OTHER PUBLICATIONS

Yi, H. et al., "Adsorption of $SO_2$, NO, and $CO_2$ on Activated Carbons: Equilibrium and Thermodynamics," Journal of Chemical Engineering Data, 59 (2014) 1556-1563.
Yin, D. et al., "Fabrication and performance of microencapsulated phase change materials with hybrid shell by in situ polymerization in Pickering emulsion," Polym. Adv. Technol. 26, (2015) 613-619.
Zhang, J. et al., "Ethylene Control Technologies in Extending Postharvest Shelf Life of Climacteric Fruit," Journal of Agricultural and Food Chemistry, 65 (2017) 7308-7319.
EthylBloc Sachets Product Sheet.
Patent Owner's Demonstrative Exhibit, Dec. 3, 2018, IPR2017-01919.
Petitioner's Demonstrative Exhibit, Dec. 3, 2018, IPR2017-01919.
*UPL Ltd.* v. *AgroFresh Inc.*, UPL Exhibit 1058, Oct. 29, 2018, IPR2017-01919.
Final Written Decision, *UPL Ltd.* v. *AgroFresh Inc.*, IPR2017-01919, Mar. 6, 2019.
Patent Owner's Request for Rehearing of Final Written Decision, *UPL Ltd.* v. *AgroFresh Inc.*, IPR2017-01919, Apr. 5, 2019.
Defendants' Opening Brief in Support of Their Omnibus Motion for Summary Judgment (Redacted Version), *AgroFresh Inc.* v. *Essentiv LLC et al.*, U.S. District Court for the District of Delaware, C. A. No. 16-662-MN.
Defendants' Concise Statement of Facts in Support of Their Omnibus Motion for Summary Judgment (Redacted Version), *AgroFresh Inc.* v. *Essentiv LLC et al.*, U.S. District Court for the District of Delaware, C. A. No. 16-662-MN.
Declaration of Karthik Kumar in Support of Their Omnibus Motion for Summary Judgment (Redacted Version), *AgroFresh Inc.* v. *Essentiv LLC et al.*, U.S. District Court for the District of Delaware, C. A. No. 16-662-MN.

\* cited by examiner

COMPLEXES OF 1-METHYLCYCLOPROPENE WITH METAL COORDINATION POLYMER NETWORKS

CROSS REFERENCE TO RELATED APPLICATION

This is a continuation of co-pending U.S. patent application Ser. No. 15/206,707, filed on Jul. 11, 2016, which claims the benefit of and priority to U.S. patent application Ser. No. 14/726,004, filed on May 29, 2015, which claims the benefit of and priority to the earlier filing date of U.S. Provisional Patent Application No. 62/077,867, filed Nov. 10, 2014, each of which is hereby incorporated by reference in its entirety.

ACKNOWLEDGMENT OF GOVERNMENT SUPPORT

This invention was made with government support under Grant Number 2014-33610-21957 awarded by the National Institute of Food and Agriculture, United States Department of Agriculture. The government has certain rights in the invention.

TECHNICAL FIELD

Embodiments relate to methods and compositions for the adsorption, storage, and handling of volatile cyclopropene compounds, such as 1-methylcyclopropene.

BACKGROUND

Cyclopropene compounds are widely used to advantageously control the effects of ethylene in plants to delay ripening and senescence, for example to extend the shelf life of harvested products. Due to the inherent volatility of cyclopropene compounds and their potential to undergo oxidation, these compounds cannot be stored in the gaseous state for long periods of time. Additionally, some cyclopropenes, such as 1-methylcyclopropene (1-MCP) gas, are flammable and pose a risk for explosion when compressed. The difficulty of storing and handling 1-MCP limits its usefulness.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

Figure 1A:
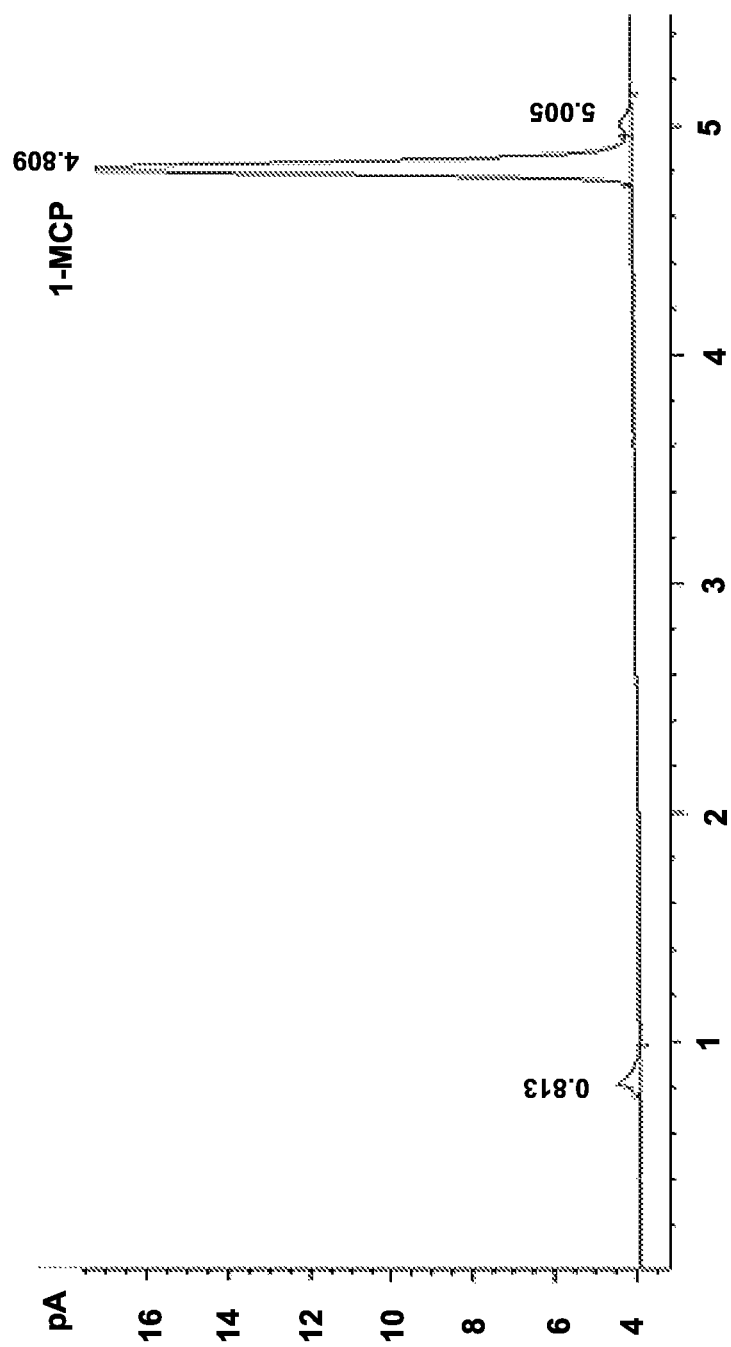
FIGS. 1A-D illustrate chromatograms of 1-MCP released by solid (FIGS. 1B and 1C) and solution (FIGS. 1A and 1D) methods for MCPN adsorption complexes (FIGS. 1B and 1D) and α-cyclodextrin molecular encapsulation complexes (FIGS. 1A and 1C), and show data corresponding to Table 2, in accordance with various embodiments.
Figure 1B:
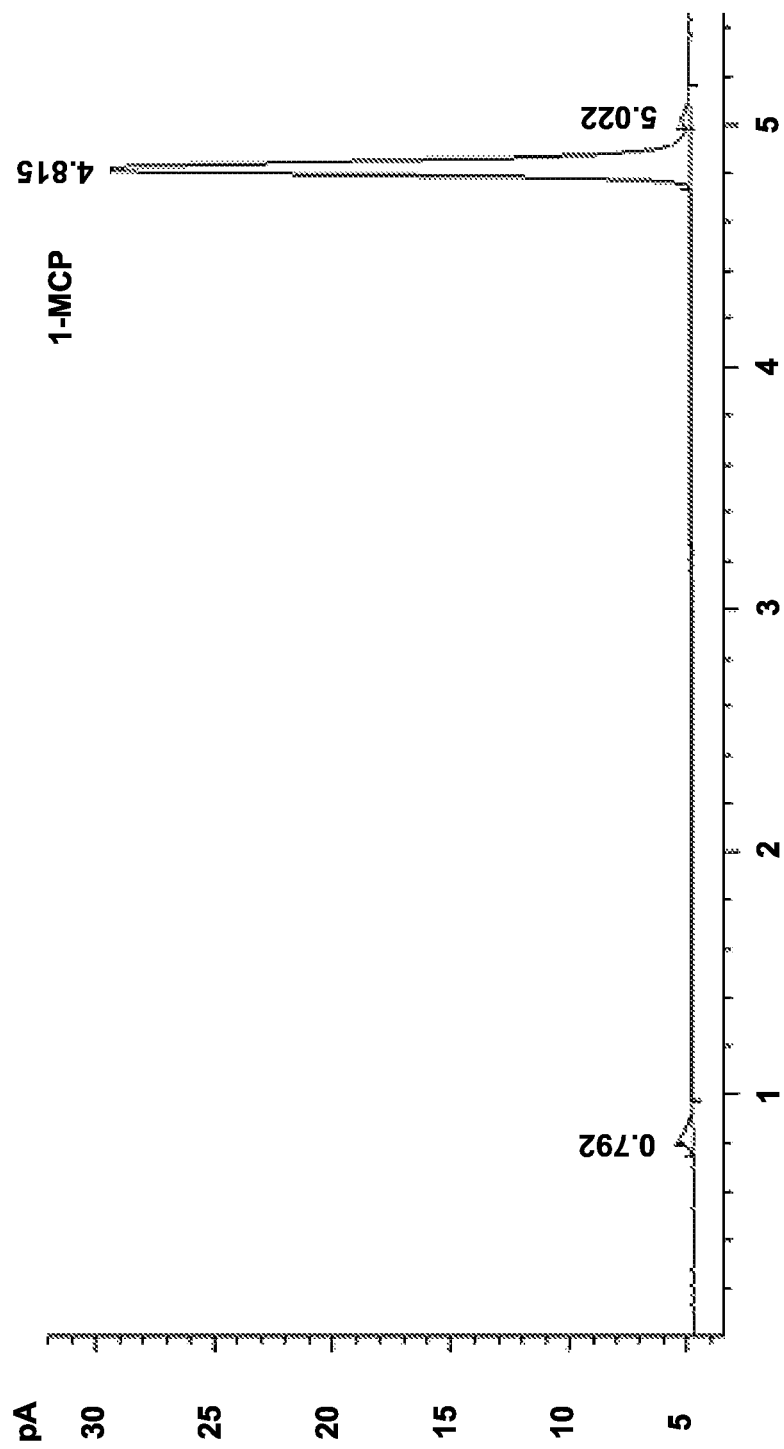
Figure 1C:
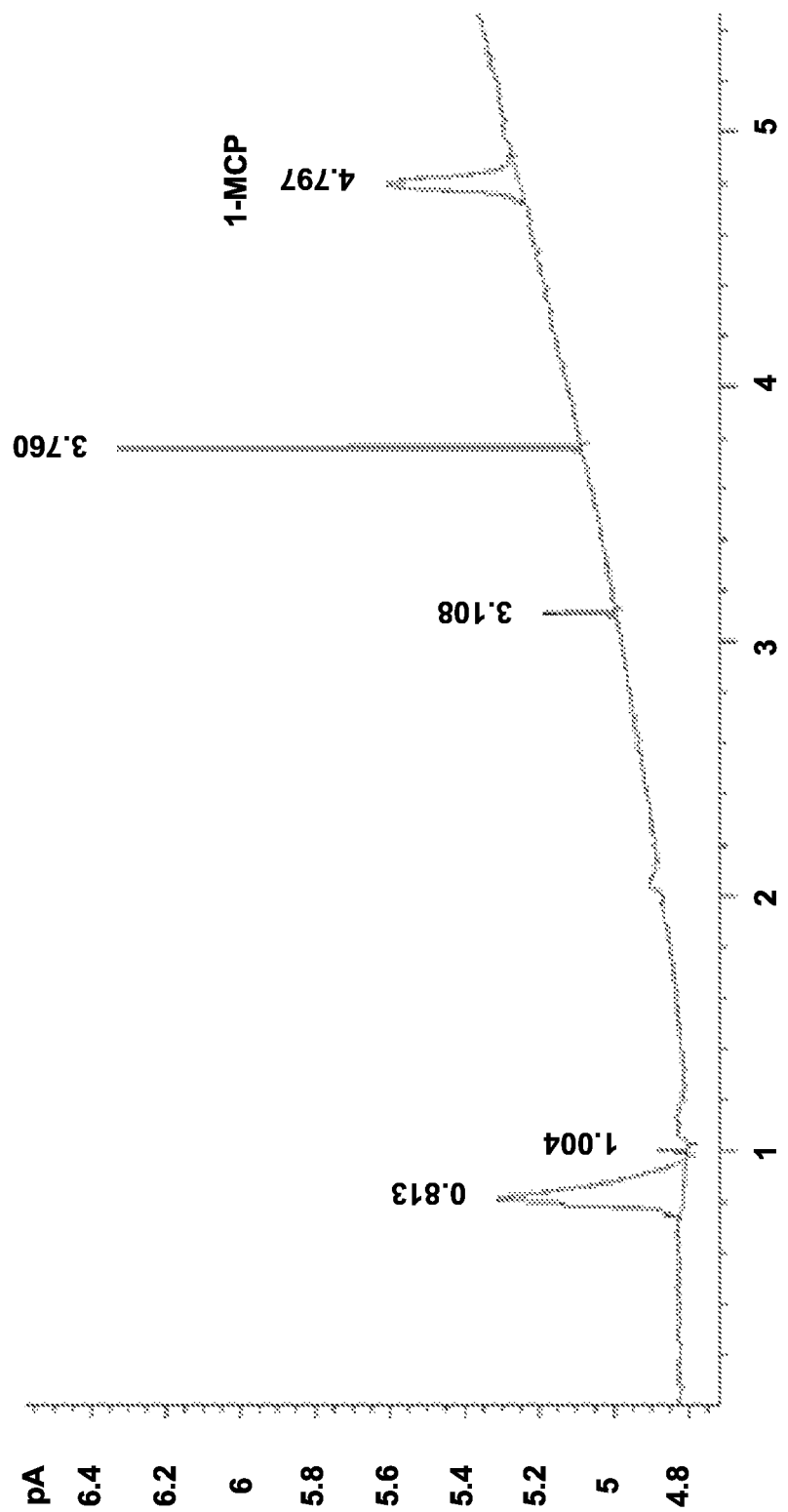

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

Terms

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

As used herein, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight. The amounts given are based on the active weight of the material.

Unless otherwise noted, technical terms are used according to conventional usage. Further, unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Adsorption: Adhesion of atoms, ions, or molecules from a gas, liquid, or dissolved solid to a surface. Adsorption is a different process from absorption whereby in absorption the molecules are taken up in the bulk of other matter, not by the surface of other matter (as with adsorption). A more general term is sorption, which covers adsorption, absorption, and ion exchange. Adsorption is distinct from molecular encapsulation, which is a specific binding process whereby a substrate selectively fits into an encapsulation site. The specificity of molecular encapsulation may include stereochemical fitting, electrostatic complementarity, and a complementary arrangement of hydrophobic and hydrogen bonding interactions.

Adsorption complex: A complex of a cyclopropene compound and a metal coordination polymer network (MCPN). For example, an adsorption complex can include 1-methylcyclopropene (1-MCP) and a metal coordination polymer network (MCPN).

Cyclopropene: An organic compound with the formula $C_3H_4$. It is the simplest cycloalkene. It has a triangular structure. Disclosed are cyclopropene compounds/derivatives, such as 1-methylcyclopropene (1-MCP; molecular formula $C_4H_6$), or other cyclopropene derivatives (Borirenes, phosphirenes, and silirenes are boron-, phosphorus-, and silicon-substituted cyclopropenes, with the formula RBC2R'2, RPC2R'2, and R2SiC2R'2, respectively) which can be adsorbed by a MCPN to form an adsorption complex.

Ethylene ($C_2H_4$): A gaseous plant hormone that affects myriad developmental processes and fitness responses in plants, such as germination, flower and leaf senescence, fruit ripening, leaf abscission, root nodulation, programmed cell death, and responsiveness to stress and pathogen attack.

Inhibit: To decrease, limit or block the action or function of a molecule. In an example, an ethylene mediated-response, such as ethylene binding to a plant ethylene receptor, is decreased, limited or blocked by a disclosed adsorption complex. For example, a disclosed adsorption complex inhibits or reduces the binding of ethylene to the ethylene receptor by at least 10%, at least 20%, at least 50%, or even at least 90%, including between about 10% to about 95%, about 20% to about 80%, about 30% to about 70%, about 40% to about 50%, such as 10%, 20%, 30%, 40%, 50%, 60%, 70%, 80%, 85%, 90%, 95%, 98%, or 100%. Such decreases can be measured using the methods disclosed herein. In particular, a disclosed adsorption complex is used to inhibit, reduce or slow fruit ripening. For example, a disclosed adsorption complex can slow or inhibit the internal concentration of naturally produced ethylene from increasing to about 0.1-1.0 (ppm).

Metal Coordination Polymeric Network (MCPN) Composition: A porous metal containing composition that is capable of adsorbing 1-MCP. A MCPN may include a metal node, such as Mg, Mn, Ca, Cu, Al, Zn, Fe, or Co, that is coupled to one or more ligands, such as an amino acid or a food additive, such as citric acid.

Permeance or permeation: The degree to which a material admits a flow of matter or transmits another substance. Permeable materials are those through which gases or liquids may pass. Permeable materials exhibit different permeances—e.g., permeation rates—for different chemical species. In this regard, permselectivity is the preferred permeation of one chemical species through a material with respect to another chemical species. Permselectivity of the desired permeate with respect to another chemical species is calculated as the ratio of the permeance of the desired permeate to the permeance of the other chemical species.

Plant: A term that refers to either a whole plant, a plant part, a plant cell, or a group of plant cells, such as plant tissue, for example.

Pore: One of many openings or void spaces in a solid substance of any kind that contribute to the substance's porosity.

Porosity is a measure of the void spaces or openings in a material, and is measured as a fraction, between 0-1, or as a percentage between 0-100%.

Porous: A term used to describe a matrix or material that is permeable to fluids. For example, a porous matrix or material is a matrix/material that is permeated by an interconnected network of pores (voids) that may be filled with a fluid (such as a liquid or gas). In some examples, both the matrix and the pore network (also known as the pore space) are continuous, so as to form two interpenetrating continua.

DESCRIPTION OF SEVERAL EMBODIMENTS

Embodiments herein provide metal coordination polymeric networks (MCPNs) that may be used to adsorb materials such as cyclopropene compounds/derivatives into the pores in their structures. Cyclopropene compounds can be used to extend the shelf life of plant products such as produce, cut flowers, and the like. For example, U.S. Pat. No. 5,518,988 describes various methods of using cyclopropene compounds to inhibit ethylene responses in plants.

One particularly effective cyclopropene for blocking ethylene receptors in plants is 1-methylcyclopropene (1-MCP), which is a volatile gas. The volatility of 1-MCP presents special challenges, since the compound cannot be stored in the gaseous state for long periods of time. Additionally, 1-MCP gas is flammable and poses a risk for explosion when compressed. The difficulties inherent in storing and handling 1-MCP limit the ways it may be used to inhibit ethylene responses in plants.

Various strategies have been employed in storing, handling, and applying 1-MCP. For instance, U.S. Pat. No. 6,017,849 discloses a method of forming complexes between 1-MCP and molecular encapsulation agents such as cyclodextrin, thereby providing a convenient means for storage and transport of these compounds. Cyclodextrins are cyclic oligosaccharides made of six or more α-D-glucopyranose units that are linked through (α-1,4)-glycosidic bonds. The chair conformations of the individual glucose unit in the ring give cyclodextrins their conical toroidal shape, with the primary hydroxyl functions of the individual sugar molecules extending from the narrow end of the torus, and the secondary hydroxyl groups from the wider end away from the internal cavity into the cone exterior. The internal cavity of the cyclodextrin torus is composed of the skeletal carbons and the ether linkage of the α-1,4-linked D-glucopyranose units giving the cyclodextrin internal cavity its lipophilic character.

A complex between 1-MCP and a cyclodextrin is formed when a single 1-MCP molecule enters the internal cavity of the cyclodextrin torus to form a complex that has been likened to a "lock and key structure" that is similar to an enzyme whereby a substrate selectively fits into the encapsulation site. Of the available cyclodextrins, α-cyclodextrin has been commercially exploited as a 1-MCP molecular encapsulation agent, but the stable complex formation of 1-MCP and β- and γ-cyclodextrins has not been achieved. Encapsulating a smaller molecule such as 1-MCP in β- or γ-cyclodextrin is challenging due to the larger internal cavities of β- and γ-cyclodextrins, which weakens the resulting complex due to an insufficiently tight "lock and key" interaction between the molecules. As α-cyclodextrin is considerably more expensive than β- and γ-cyclodextrins, molecular encapsulation of 1-MCP with α-cyclodextrin may be costly.

By contrast, the MCPNs disclosed herein are a less costly option for sequestering 1-MCP for safe handling and use, and more options are available, since a "lock and key" type size-based fit is not required with an adsorption-based complexation process. Generally speaking, the MCPNs for use in various embodiments disclosed herein include any porous MCPN composition that is capable of adsorbing 1-MCP. In various embodiments, the MCPN may include a metal node that is coupled to one or more ligands. For instance, in various embodiments, the metal node may be Mg, Mn, Ca, Cu, Al, Zn, Fe, or Co. In some embodiments, the ligand may be an amino acid or a food additive, such as citric acid. In some embodiments, a MCPN is any porous MCPN composition capable of adsorbing 1-MCP, but does not include cyclodextrin or derivatives thereof. In some embodiments, a MCPN is any porous MCPN composition capable of adsorbing 1-MCP, but does not form a lock and key structure with 1-MCP.

In some embodiments, the MCPN may be a calcium coordination polymer network. One specific, non-limiting example of a calcium coordination polymer network that may be used is [Ca(4,4'-sulfonyldibenzoate)].$H_2O$. Other specific, non-limiting examples of MCPNs for use in various embodiments include Cu-TDPAT, also referred to as 2,4,6-tris(3,5-dicarboxylphenylamino)-1,3,5-triazine, $Zn_2$(tcbpe), also referred to as the reaction product of tetra-(4-bromophenyl)ethylene (tpe-Br) and 4-(methoxycarbonyl) phenylboronic acid, [$Co_3$(biphenyldicarboxylate)$_3$4,4'bipyridine]. 4DMF.$H_2O$, [Co(biphenyldicarboxylate)(4,4'bipyridine)]. 0.5DMF, [$Zn_2$(biphenyldicarboxylate)$_2$(1,2-bipyridylethene)].2DMF, $Mg_3(O_2C$—$C_{10}$—$H_6$—$CO_2)_3$, magnesium formate, aluminum terephthalate, $Cu_3$(benzene-1,3,5-tricarboxylate)$_2$, Fe(1,3,5-benzenetricarboxylate), 2-methylimidazole zinc salt, Co(2-methylimidazole)$_2$, and Al(OH)fumarate.

The MCPNs listed above are solids synthesized in a solvent (such as DMF and water). In various embodiments, after the network is formed, the solvent may be driven off by heating. For instance, in various embodiments, the MCPN materials may be activated with heat to remove all moisture or solvents before use.

Adsorption of 1-MCP by the MCPNs may be carried out in a variety of ways, including both solid-based methods and solution-based methods, as disclosed herein in various embodiments. In various embodiments, the general protocol in both methods may include a dual-vessel system, wherein 1-MCP is generated in the first vessel, also referred to as the generation vessel, and the adsorption takes place in the second vessel, also referred to as the adsorption vessel. In some examples, before adsorption, the adsorbent may first be dried in a vacuum oven and sealed in the adsorption vessel. 1-MCP may be generated in the generation vessel and introduced to the adsorption vessel for adsorption by the MCPN. In various embodiments, the adsorption may be carried out with continuous agitation of the adsorbent.

In various embodiments, once the 1-MCP has been adsorbed by the MCPN, the MCPN-1-MCP complexes may be formed into tablets or other unit formulations for ease of use. For example, in some embodiments, tablets containing MCPN may be made using starch or starch like materials, while in other embodiments they may also include food grade starch such as corn starch or other modified starches (e.g., dextrin, acetylated starch, alkaline modified starch, carboxy methylated starch, and acetylated oxidized starch). In some embodiments, the starches may be quick and easy-gelling starches having aqueous-based materials, or they may be slow-gelling. In some embodiments, the tablets or other unit formulations may include other filler materials, such as inert materials, such as clay, that have the ability to slowly swell or disintegrate with the addition of aqueous based material (e.g., kaolin clay). Other fillers may include gums such as xanthan gum (CP Kelko, Atlanta, Ga.), carboxy methyl cellulose (CP Kelko, Atlanta, Ga.), carageenan (CP Kelko, Atlanta, Ga.), hydroxyl propyl cellulose (CP Kelko, Atlanta, Ga.), and hydroxyl ethyl cellulose (CP Kelko, Atlanta, Ga.).

In various embodiments, the tablets may be coated. Specific, non-limiting examples of coating materials include polymethacrylates, cellulose-based polymers (e.g., cellulose acetate phthalate or hydroxypropylmethylcellulose phthalate), polyvinyl derivatives (e.g., polyvinyl acetate phthalate), and other copolymers (e.g, half esters of the copolymerisate of styene and maleic acid). In various embodiments, other ingredients in the coating material may include plasticizers, anti-adhesion agents, colorants or pigments, solubilizers or dispersion agents, and other additives.

In some embodiments, the MCPN-1-MCP complexes may be contained within capsules. Specific, non-limiting examples of capsules for use in accordance with various embodiments include gelatin capsules and hydroxylpropyl methylcellulose capsules (Capsugel, Morristown, N.J.). In various embodiments, suitable capsules also may include any material that has low gas permeability properties, but that may permeate water vapor, such as nylon or PVOH-based capsules, or any other starch or gum based capsules (e.g., carboxymethylcellulose).

In some embodiments, coatings for capsules also may be used. For example, in specific, non-limiting examples, the coating materials may include polymethacrylates, cellulose-based polymers (e.g., cellulose acetate phthalate and hydroxypropylmethylcellulose phthalate), polyvinyl derivatives (e.g., polyvinyl acetate phthalate), and other copolymers (e.g., half esters of the copolymerisate of styene and maleic acid). Other ingredients in the coating materials may include plasticizers, anti-adhesion agents, colorants or pigments, solubilizers or dispersion agents, and other additives.

In various embodiments, the capsules may include fillers inside the capsules, hereinafter referred to as capsule fillers, which may include 100% non-aqueous material, or non-aqueous containing less than 2% aqueous material, that disperses the MCPN-1-MCP complex, minimizes the loss of 1-MCP, and achieve at least 90% active ingredient retention in the formulation, when no heat, pressure or aqueous based solution such as water is used for releasing the active ingredient. Specific, non-limiting examples of non-aqueous (or less than 2% aqueous) materials include hydrophobic/non-aqueous liquids, such as mineral oil or other plant based oils, polyols, (e.g., glycerol, 99.9% pure, 0.1% water, Sigma Aldrich Co., St. Louis, Mo.) and D-sorbitol (98% pure, Sigma Aldrich Co., St. Louis, Mo.). Other polyols that may be used include di-, tri-, and tetrols and other sugar alcohols, and/or mixtures thereof. Other specific, non-limiting examples of capsule fillers include gums that have the ability to hydrate with addition of aqueous solution or water vapor, such as xanthan gum (CP Kelko, Atlanta, Ga.), carboxy methyl cellulose (CP Kelko, Atlanta, Ga.), carageenan (CP Kelko, Atlanta, Ga.), hydroxyl propyl cellulose (CP Kelko, Atlanta, Ga.), and hydroxyl ethyl cellulose (CP Kelko, Atlanta, Ga.). Other specific, non-limiting examples of capsule fillers include starches (e.g., food grade starch such as corn starch) or other modified starches (e.g., dextrin, acetylated starch, alkaline modified starch, carboxy methylated starch, and acetylated oxidized starch). In various embodiments, the capsule fillers may also be used directly for application to the plant or plant-based material as a liquid formulation for drenching or spraying.

In various embodiments, the MCPNs that are for capsule fillers or liquid formulations may have a particle size with a lower limit of at least 0.05 mm, such as 0.10 mm or higher. In various embodiments, such MCPNs may have an upper size limit of 5 mm or lower, such as 3 mm or lower or 1.5 mm or lower.

Various methods may be used for releasing the 1-MCP from the MCPN-1-MCP complex, for example, for treating plants or plant parts to inhibit an ethylene response. In some embodiments, the MCPN-1-MCP complex may be contacted with water, which may break open the structure of the MCPN. In various embodiments, this may cause the 1-MCP to be released as a gas, which may then be applied to or directed to the desired plant materials in a closed environment.

In other embodiments, heat or pressure may be used to release 1-MCP from the MCPN-1-MCP complex in order to inhibit an ethylene response in a plant or plant parts. In various embodiments, the 1-MCP release temperature may be about 35° C. or higher, such as 50° C. or higher. In various embodiments, the upper limit for releasing 1-MCP from the MCPN-1-MCP complex may be about 100° C. or lower, such as 80° C. or lower or 60° C. or lower. In various embodiments, although temperatures higher than these cut-off values may be used to release 1-MCP from the MCPN-1-MCP complex (MCPNs generally are thermo-stable up to about 575° C.) in some embodiments, significant degradation of 1-MCP may take place above 60° C., which may affect the biological activity of 1-MCP. In embodiments wherein pressure is used to release the 1-MCP from the MCPN-1-MCP complex, the release pressure generally, is about 5 millibars or higher, such as 10 millibars or higher or 15 millibars or higher. In various embodiments, the upper limit for release pressure may be a package internal pressure of 400 millibars or lower, such as 300 millibars or lower, 200 millibars or lower, or 100 millibars or lower. Although exemplary temperature and pressure ranges are provided, one of skill in the art will appreciate that by other techniques or modifications may be employed to aid in the release of 1-MCP from the MCPN-1-MCP complex.

In various embodiments, MCPN-1-MCP complex sachets may be used, for instance in certain applications in box, pallet, refrigerator container, or storage room applications. In various embodiments, the inherent 1-MCP and moisture transmission characteristics of the polymeric film (or portion thereof) forming the exterior of the sachets may be characterized, such as the properties of the film itself, in the absence of any perforations or other alterations which may be included to aid in 1-MCP release. For instance, in some embodiments, the composition of a film may be characterized by characterizing the moisture transmission characteristics of the film using a standard film thickness, such as a film having a thickness of about 25.4 micrometers. For films having different thicknesses than the standard thickness (e.g., from 8 to 76.2 micrometers), one of skill in the art could easily and accurately calculate the equivalent moisture transmission characteristics of a film having the same composition, but having a standard thickness of 25.4 micrometers or 1 mil., for instance to compare moisture transmission characteristics of two films having different thicknesses. In various embodiments, the 1-MCP or moisture transmission rate of a film having thickness of 25.4 micrometers is labeled "FL-1" herein.

Specific, non-limiting examples of film compositions for use in various embodiments are those in which the FL-1 for 1-MCP transmission at 23° C., in units of $cm^3/(m^2\text{-day})$, is 800 or higher; such as 4,000 or higher, 5,000 or higher, 10,000 or higher, or 20,000 or higher. Other specific, non-limiting examples of film compositions for use in various embodiments include films with FL-1 for 1-MCP transmission at 23° C., in units of $cm^3/(m^2\text{-day})$, may be 150,000 or lower, such as 80,000 or lower or 60,000 or lower. In specific, non-limiting examples, films for use in various embodiments may be films with FL-1 for water vapor at 37.8° C., in units of $g/(m^2\text{-day})$, such as 5 or higher, or 25 or higher. In other specific, non-limiting examples, films for use in various embodiments may be films with FL-1 for water vapor at 37.8° C., in units of $g/(m^2\text{-day})$, of 350 or lower, such as 200 or lower, or 100 or lower.

In various embodiments, some or all of the interior and exterior surface of the sachets may be polymeric. In various embodiments, the polymer may be a polymeric film or coating. In some embodiments, the polymeric film or coating layers for use in various embodiments may have an average thickness of 1 micrometer or more, such as 5 micrometers or more, or 10 micrometers or more. In some embodiments, the polymeric film or coating layers for use in various embodiments may have an average thickness of 250 micrometers or less, such as 200 micrometers or less, 100 micrometers or less, or 75 micrometers or less.

In some embodiments, the amount of adsorbed 1-MCP present in the overall composition of the MCPN-1-MCP complex may be 0.001% by active ingredient (a.i.) weight or more, such as 0.005% by a.i. weight or more, or 0.05% by a.i. weight or more. In some embodiments, the amount of adsorbed 1-MCP present in the overall composition of the MCPN-1-MCP complex may be 25% by a.i. weight or less, such as 20% by a.i. weight or less, or 15% by a.i. weight or less.

In some embodiments, the MCPN may have a total porosity of 0.001% by volume or more, such as 0.005% by volume or more, or 0.05% by volume or more. In some embodiments, the MCPN may have a total porosity of 50% by volume or less, such as 40% by volume or less, or 25% by volume or less.

In some embodiments, the MCPN may have the ability to break down the coordination network in water.

EXAMPLES

Example 1: Synthesis of 1-MCP

This example describes one exemplary method for the synthesis of 1-MCP. 1-MCP was generated from a 1-MCP- Li suspension in mineral oil, which was prepared by reacting lithium diisopropylamide (LDA) with 3-chloro-2-methylpropene under a nitrogen environment which is described in "Kinetics of Molecular Encapsulation of 1-Methylcyclopropene into α-Cyclodextrin," *Journal of Agricultural and Food Chemistry*, 2007, 55(26): p. 11020-11026, which is incorporated herein by reference. Table 1 summarizes the reaction conditions used to synthesize 1-MCP.

TABLE 1

Reaction conditions to synthesize 1-MCP

| | |
|---|---|
| Reaction mixture component | LDA:3-chloro-2-methylpropene = 4:1 (molar ratio) |
| Reaction temperature | Ambient temperature (23° C.) |
| Reaction time | 1.5 hours |
| Yield (based on 1 mol of 3-chloro-2-methylpropene) | 60% (0.6 mol of 1-MCP) |

Example 2: MCPNs and their Synthesis

This Example provides specific examples of MCPNs for use in various embodiments and methods of their synthesis. In some embodiments, the MCPN may be a calcium coordination polymer network. One specific, non-limiting example of a calcium coordination polymer network that may be used is [Ca(4,4'-sulfonyldibenzoate)].$H_2O$. The synthesis and structural properties of [Ca(4,4'-sulfonyldibenzoate)].$H_2O$ are described in "A Calcium Coordination Framework Having Permanent Porosity and High $CO_2/N_2$ Selectivity," Banerjee et al., *Crystal Growth and Design*, 2012, 2162-2165, which is incorporated herein by reference in its entirety. Briefly, in one specific example, [Ca(4,4'-sulfonyldibenzoate)].$H_2O$ was synthesized according to the following protocol: a mixture of 0.0006 moles of $CaCl_2$ (0.074 g) and 0.0006 moles of 4,4'-SDB (0.198 gram) were dissolved in 10.05 gram of ethanol and stirred for 2 hours to achieve homogeneity [molar ratio of metal chloride:ligand:solvent=1:1:380]. The resultant solution was heated at 180° C. for 5 days. Colorless needle shaped crystals were recovered as products and washed with and ethanol (Yield: 50% based on calcium in anhydrous $CaCl_2$, 0.112 gram). The water in the final product was derived from the 95% ethanol solvent and adsorbed moisture in the $CaCl_2$ reactant.

In other embodiments, the MCPN may be Cu-TDPAT, also referred to as 2,4,6-tris(3,5-dicarboxylphenylamino)-1,3,5-triazine. The synthesis and structural properties Cu-TDPAT are described in "Stability and Hydrogen Adsorption of Metal Organic Frameworks Prepared via Different Catalyst Doping Methods," Wang et al., *Journal of Catalysis*, 2014. 318(0): p. 128-142, which is incorporated herein by reference in its entirety. In one specific, non-limiting example, crystals of Cu-TDPAT were grown by a reaction of 0.68 mmol $Cu(NO_3)_2.6H_2O$, 0.05 mmol $H_6TDPAT$ in 2 mL DMA (dimethylacetamide), 2 mL DMSO (dimethyl sulfoxide), 0.2 mL $H_2O$ and 0.9 mL $HBF_4$ at 358 K for three days. The blue polyhedron crystals ([$Cu_3(TDPAT)(H_2O)_3$].10$H_2O$.5DMA) were collected and then washed with 10 mL DMA three times. Methanol exchange was carried out every 1 hour during daytime for one week for solvent exchange.

In other embodiments, the MCPN may be $Zn_2$(tcbpe), also referred to as the reaction product of tetra-(4-bromophenyl)ethylene (tpe-Br) and 4-(methoxycarbonyl) phenylboronic acid. A typical synthesis of $Zn_2$(tcbpe) is as follows: $Zn(NO_3)_2.6H_2O$ (0.0892 gram, 0.30 mmol), $H_4$tcbpe (0.0244 gram, 0.03 mmol), and N,N'-dimethylacetamide (DMA, 2 mL) are loaded into a 20 mL glass vial. The glass vial is capped and sonicated at room temperature for a few minutes until a clear solution is obtained. The sealed glass vial is then placed at 120° C. for reaction of 48 hours. Transparent light yellow single crystals are harvested through filtration, washed with DMA, and dried in air.

In other embodiments, the MCPN may be [$Co_3$(biphenyldicarboxylate)$_3$4,4'bipyridine].4DMF.$H_2O$. The synthesis and properties of [$Co_3$(biphenyldicarboxylate)$_3$4,4'bipyridine].4DMF.$H_2O$ are described in "A Recyclable Nanoporous Material Suitable for Ship-In-Bottle Synthesis and Large Hydrocarbon Sorption," Long Pan et al., *Angew. Chem. Int. Ed.* 2003, 42, No. 5, pp. 542-546, which is incorporated herein by reference in its entirety. In this publication, [$Co_3$(biphenyldicarboxylate)$_3$4,4'-bipyridine].4DMF.$H_2O$ is referred to as [$Co_3$(bpdc)$_3$bpy].4DMF.$H_2O$, wherein bpdc is biphenyldicarboxylate and bpy is 4,4'-bipyridine, and DMF refers to N,N-dimethylformamide.

In another embodiment, the MCPN may be [Co(biphenyldicarboxylate)(4,4'bipyridine)].0.5DMF. The synthesis and properties of [Co(biphenyldicarboxylate)(4,4'bipyridine)].0.5DMF are described in "A Recyclable Porous Material with Unusual Adsorption Capability: Self Assembly via Structural Transformations," Long Pan et al., *Chem. Commun.*, 2003, pp. 854-855, which is incorporated herein by reference in its entirety. In this publication, [Co(biphenyldicarboxylate)(4,4'-bipyridine)].0.5DMF is referred to as [Co(bpdc)(bpy)].0.5DMF.

In another embodiment, the MCPN may be [$Zn_2$(biphenyldicarboxylate)$_2$(1,2-bipyridylethene)].2DMF. The synthesis and properties of [$Zn_2$(biphenyldicarboxylate)$_2$(1,2-bipyridylethene)].2DMF are described in "A Multifunctional Microporous MOF with Recyclable Framework and High $H_2$ Binding Energy", Anjian Lan et al., *Inorg. Chem.* 2009, 48, pp. 7165-7173, and in "A Luminescent Microporous Metal-Organic Framework for the Fast and Reversible Detection of High Explosives," Anjian Lan, *Angew. Chem. Int. Ed.* 2009, 48, pp. 2334-2338, both of which are incorporated herein by reference in their entirety. In the latter reference, [$Zn_2$(biphenyldicarboxylate)$_2$(1,2-bipyridylethene)].2DMF is referred to as [$Zn_2$(bpdc)$_2$(bpee)].2DMF, wherein bpee is 1,2-bipyridylethene.

In another embodiment, the MCPN may be $Mg_3(O_2C-C_{10}-H_6-CO_2)_3$. The synthesis and properties of $Mg_3(O_2C-C_{10}-H_6-CO_2)_3$ are described in "Strong $H_2$ Binding and Selective Gas Adsorption within the Microporous Coordination Solid $Mg_3(O_2C-C_{10}-H_6-CO_2)_3$," Mircea Dinca et al., *J. Am. Chem. Soc.*, 2005, 127, pp. 9376-9377, which is incorporated herein by reference in its entirety.

In another embodiment, the MCPN may be Magnesium Formate. The synthesis and properties of Magnesium Formate are described in "Phase Transitions and $CO_2$ Adsorption Properties of Polymeric Magnesium Formate," Andrea Rossin et al., *Crystal Growth & Design*, 2008, 8(9), pp 3302-3308, which is incorporated herein by reference in its entirety.

In another embodiment, the MCPN may be aluminum terephthalate. The synthesis and properties of aluminum terephthalate are described in "A Rationale for the Large Breathing of the Porous Aluminum Terephthalate (MIL-53) Upon Hydration," Loiseau et al., *Chemistry—A European Journal*, 2004, 10(6): pp. 1373-1382, which is incorporated herein by reference in its entirety.

In another embodiment, the MCPN may be $Cu_3$(benzene-1,3,5-tricarboxylate)$_2$. The synthesis and properties of $Cu_3$(benzene-1,3,5-tricarboxylate)$_2$ are described in "Argon Adsorption on $Cu_3$(Benzene-1,3,5-tricarboxylate)$_2(H_2O)_3$ Metal Organic Framework," Krungleviciute et al., *Langmuir*, 2007. 23(6): pp. 3106-3109, which is incorporated herein by reference in its entirety.

In another embodiment, the MCPN may be Fe(1,3,5-benzenetricarboxylate). The synthesis and properties of Fe(1,3,5-benzenetricarboxylate) may be found in "Complexes of Iron(III) Salen and Saloph Schiff Bases with Bridging Dicarboxylic and Tricarboxylic Acids," Kopel, et al., *Transition Metal Chemistry*, 1998. 23(2): pp. 139-142, which is incorporated herein by reference in its entirety.

In another embodiment, the MCPN may be 2-Methylimidazole Zinc salt. The synthesis and properties of 2-Methylimidazole Zinc salt are described in "A Two-Dimensional Zeolitic Imidazolate Framework with A Cushion-Shaped Cavity for $CO_2$ Adsorption," Chen et al., *Chemical Communications*, 2013. 49(82): pp. 9500-9502, which is incorporated herein by reference in its entirety.

In another embodiment, the MCPN may be Co(2-methylimidazole)$_2$. The synthesis and properties of Co(2-methylimidazole)$_2$ are described in "Hydrothermal Synthesis of Zeolitic Imidazolate Framework-67 (ZIF-67) Nanocrystals," Qian et al., *Materials Letters*, 2012. 82(0): pp. 220-223, which is incorporated herein by reference in its entirety.

In another embodiment, the MCPN may be Al(OH) fumarate. The synthesis and properties of Al(OH)fumarate are described in "The Structure of the Aluminum Fumarate Metal-Organic Framework A520," Alvarez et al., *Angewandte Chemie*, 2015, 127(12): pp. 3735-3739, which is incorporated herein by reference in its entirety.

Example 3: Adsorption of 1-MCP in MCPN

This Example provides specific examples of methods for adsorbing 1-MCP into a MCPN. Adsorption of 1-MCP was carried out using both a modified solid method (method A) and a solution-based method (method B), as disclosed herein. The general protocol in both methods included a dual-vessel system, where 1-MCP was generated in the first vessel, also referred to as the generation vessel, and the adsorption took place in the second vessel, also referred to as the adsorption vessel. Before adsorption, 50 mg of adsorbent was first dried in a vacuum oven at 100° C. overnight and sealed in the adsorption vessel. About 0.1 atm pressure (100,000 ppm headspace concentration) of 1-MCP was generated in the generation vessel and introduced to the adsorption vessel. The adsorption was continued for 20 hours with continuous agitation of the adsorbent.

During solid-based adsorption with MCPN, 50 mg of dry adsorbent was used for adsorption purposes, and during solution-based adsorption with MCPN, 1 mg/mL concentration of MCPN solution was prepared with distilled water in the generation vessel.

In another example, the specific MCPN selected was CaSDB. A two-jar setup was used essentially as described above. Briefly, 1-MCP was generated in one jar and the adsorption took place in the other jar. 0.05 g of CaSDB was first activated (dried in a vacuum oven at 100° C. overnight) and placed in the adsorption jar in which a vacuum was created by a vacuum pump. In the other jar, lithium salt was mixed with water to generate 1-MCP (headspace concentration>0.1 atm or 100,000 ppm). The two jars (1-MCP generation jar and the adsorption jar) were then connected to introduce 1-MCP into the encapsulation jar. The 1-MCP adsorption continued for 20 hours.

Example 4: Adsorbents (MCPNs) and Encapsulants (Cyclodextrins)

This Example illustrates some of the MCPNs of the present disclosure and prior art encapsulants (cyclodextrins). The adsorbents (MCPNs) include calcium-4,4'-sulfonyldibenzoic acid (S1), copper-2,4,6-tris(3,5-dicarboxylphenylamino)-1,3,5-triazine (S2), and zinc-tcbpe (reaction product of tetra-(4-bromo-phenyl)ethylene (tpe-Br) and 4-(methoxycarbonyl)phenylboronic acid) (S3). For comparison, cyclodextrin encapsulants, such as alpha-(S4) and beta-(S5) cyclodextrin, were also used.

Example 5: Encapsulation of 1-MCP in α-Cyclodextrin

This Example describes the methods used for the encapsulation of 1-MCP in α-cyclodextrin (e.g., for comparison to 1-MCP adsorbed into MCPNs). A jar-in-jar setup was designed that represented a modified and simplified version of the method described in "Kinetics of Molecular Encapsulation of 1-Methylcyclopropene into α-Cyclodextrin," *Journal of Agricultural and Food Chemistry*, 2007, 55(26): p. 11020-11026. Briefly, 0.3 g of α-cyclodextrin powder was dissolved in 2 ml of water in a small glass jar (75 mL). Lithium salt was mixed with water in a bigger jar (200 mL) to generate 1-MCP (headspace concentration>0.1 atm or 100,000 ppm). The small jar containing the α-cyclodextrin solution was placed into the bigger jar, which was then closed immediately and placed on a shaker for 15 hours. The encapsulation complex precipitated out from the solution and the precipitate was filtered and dried.

Example 6: Adsorption Levels in Complexes Formed Between 1-MCP and MCPNs vs. Encapsulation Levels with Cyclodextrins This Example illustrates some of the differences between the MCPNs of the present disclosure and prior art encapsulants (cyclodextrins). Adsorption of 1-MCP using method A and method B was carried out in S1 and compared with the encapsulation level in S4. Method B for S4 encapsulation was modified by making a solution in a pH 4.6 buffer solution to form concentration of 50 mg S4/mL (method D) (Neoh et al., "Kinetics of Molecular Adsorption of 1-Methylcyclopropene into α-Cyclodextrin," *Journal of Agricultural and Food Chemistry*, 2007; 55(26): p. 11020-11026). The samples were taken out after solution adsorption (A1)/ encapsulation (E4), filtered, and allowed to dry to remove excess water. The percentage adsorbed or encapsulated was quantified by taking 55 mg of A1 or E4 and mixed with 25 ml of water in 500 ml sealed glass bottles to release 1-MCP.

Headspace sample was collected and injected into gas chromatography using methods described in Mir, "Harvest Maturity, Storage Temperature and 1-MCP Application Frequency Alter Firmness Retention and Chlorophyll Fluorescence of "Redchief Delicious" Apples," *Journal of American society of horticultural science*, 2001, 126(5): 618-624). 1-MCP was identified as the peak at the retention time of 4.8 minutes. The peak area was used to quantify the concentration.

The results of this procedure are shown in Table 2. Adsorption in S1 using both method A and B and encapsulation in S4 using solution method D achieved similar adsorption or inclusion level (~2.5%), but inclusion level in S4 using method A was negligible (0.05%).

TABLE 2

Adsorption or inclusion level of 1-MCP in S1 and S4 using method A and method B

| Sample | Adsorption or inclusion level % |
|---|---|
| S1 Method A | 2.52 |
| S1 Method B | 2.74 |
| S4 Method A | 0.05 |
| S4 Method D | 2.46 |

Figure 1D:
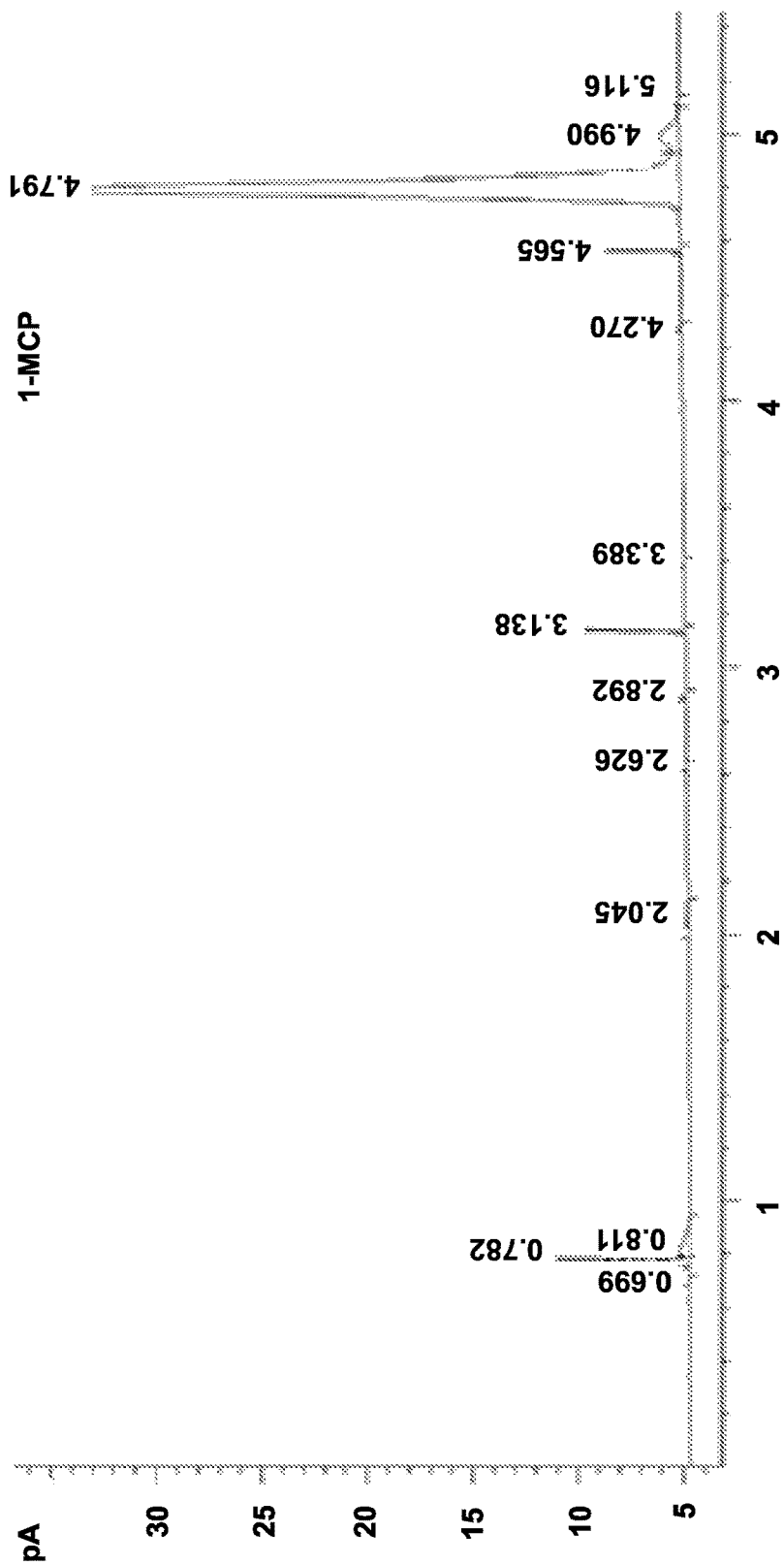

FIGS. 1A-D illustrate chromatograms of 1-MCP released by solid (FIGS. 1B and 1C) and solution (FIGS. 1A and 1D) methods for MCPN adsorption complexes (FIGS. 1B and 1D) and α-cyclodextrin molecular encapsulation complexes (FIGS. 1A and 1C), and show data corresponding to Table 2, in accordance with various embodiments. The chromatograms in FIG. 1 show that the 1-MCP released from MCPN by both methods A (FIG. 1A) and B (FIG. 1B) produced 1-MCP peaks at 4.8 min. The peak areas further illustrate that adsorption in S1 using both method A and B and encapsulation of S4 using solution method D (FIG. 1D) achieved similar inclusion levels (~2.5%), but the inclusion level in S4 using method A (FIG. 1C) was negligible (0.05%). Additionally, the chromatogram in FIG. 1D shows some impurity peaks in addition to the 1-MCP peak.

Example 7: Adsorption Levels with Various Adsorption Methods in Various MCPNs

This Example shows the adsorption levels of several samples of MCPNs. Adsorption of 1-MCP was carried out in Samples S1, S2 and S3 using method A. Table 3 shows that the adsorption levels in S1 and S3 were 2.5% and 0.3%, respectively, and there was no adsorption in S2.

TABLE 3

Adsorption level of 1-MCP in S1, S2 and S3 using method A

| Sample | Adsorption level (%) |
|---|---|
| S1 | 2.52 |
| S2 | 0 |
| S3 | 0.3 |

Figure 2:
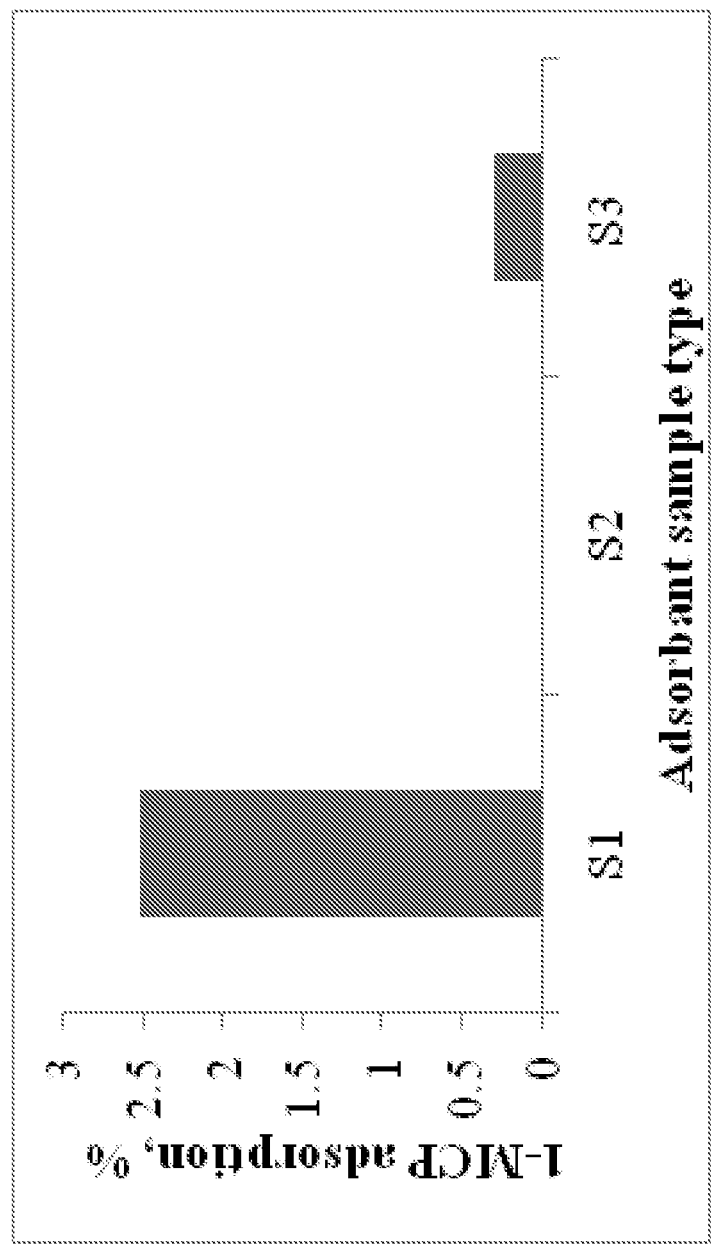
FIG. 2 is a bar graph illustrating inclusion levels of 1-MCP in various MCPNs (S1, S2 and S3) using a solid adsorption method, and shows data corresponding to Table 3, in accordance with various embodiments.

FIG. 2 is a bar graph illustrating inclusion levels of 1-MCP in various MCPNs (S1, S2 and S3) using a solid adsorption method, and shows data corresponding to Table 3, in accordance with various embodiments. The adsorption levels of 1-MCP using adsorption method A in S1 and S3 were 2.5% and 0.3%, respectively, and there was no adsorption in S2.

Example 8: Release Rate of 1-MCP

This Example illustrates the release rate of 1-MCP from MCPNs and cyclodextrins. Release rate of 1-MCP was compared between samples S1 and S4. Adsorption of 1-MCP in sample S1 was carried out using both methods A and B. Encapsulation of sample S4 was carried out using methods A and D. Method C was used for the release of 1-MCP, where about 25 mg of S1 and S4 were hydrated with 25 mL of water in a 500 mL glass bottle under agitation. Headspace samples were withdrawn periodically to quantify the released 1-MCP.

1-MCP release from S1 method B was instantaneous and complete release was achieved within 5 minutes. Similarly S4 encapsulated by method A released 1-MCP almost instantaneously. As shown in Table 4, 1-MCP release from S1 method A and S4 method D was in a slow manner, and the complete release was achieved within 60 and 40 minutes respectively.

TABLE 4

Release of 1-MCP from S1 (method A) and S4 (method D)

| S1 (Method A) | | S4 (Method D) | |
|---|---|---|---|
| Time (min) | % Released | Time (min) | % Released |
| 15 | 35 | 5 | 39 |
| 30 | 76 | 15 | 62 |
| 45 | 94 | 25 | 84 |
| 60 | 100 | 40 | 100 |
| 75 | 100 | 60 | 100 |

Figure 3:
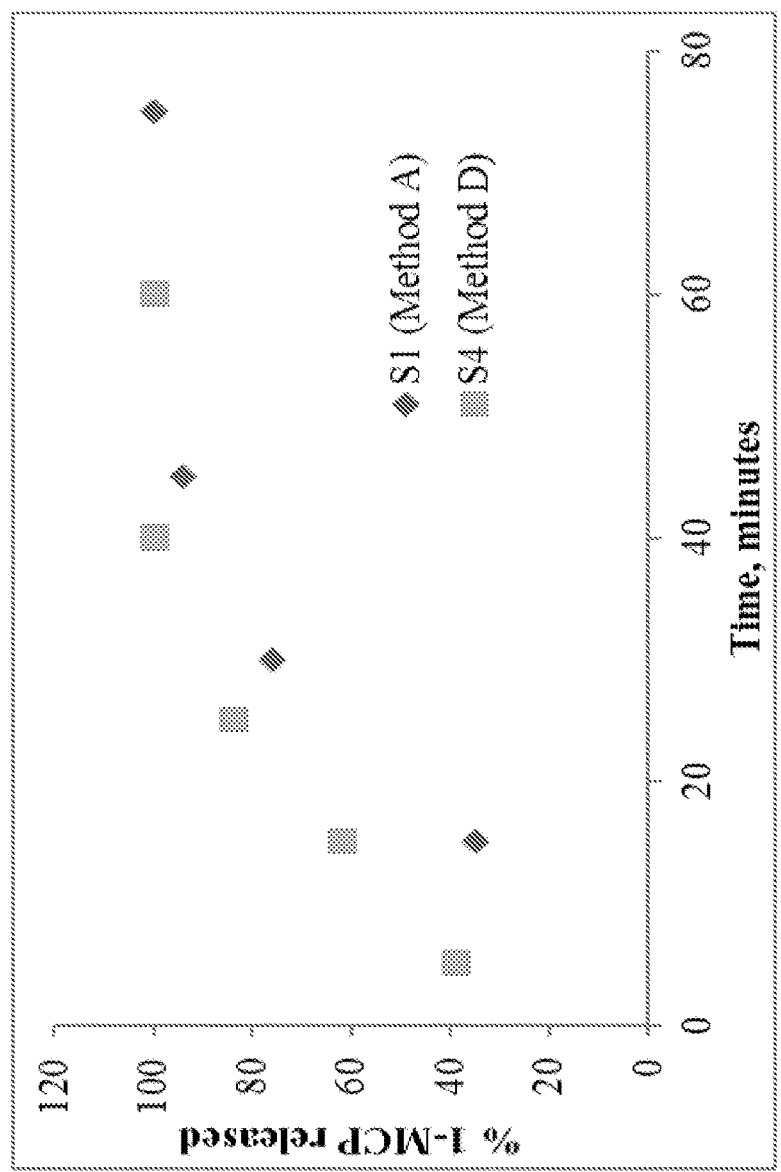
FIG. 3 is a graph illustrating the release of 1-MCP by suspending the encapsulant and the absorbent complexes in water from S1 (method A) and S4 (method D), and shows data corresponding to Table 4, in accordance with various embodiments.

FIG. 3 is a graph illustrating the release of 1-MCP by suspending the encapsulant and the absorbent complexes in water from S1 (method A) and S4 (method D), and shows data corresponding to Table 4, in accordance with various embodiments. The 1-MCP release from S1 method A and S4 method D occurred in a slow manner, and the complete release was achieved within 60 and 40 minutes, respectively. The release from adsorbent S1 was slightly slower than that of encapsulant S4. The release from S1 was 27% less at 15 minutes, 8% in 25 minutes and 6% in 40 minutes compared to encapsulant S4.

Example 9: Release Rate of 1-MCP from Samples S1 and S4

This example illustrates a comparison of the release rates of 1-MCP from an MCPN and a cyclodextrin. The release rate of 1-MCP was compared between samples S1 and S4 after adsorption and inclusion of 1-MCP. Adsorption of 1-MCP in sample S1 was carried out using method A (AS1). Encapsulation of sample S4 was carried out using method D (ES4). Method E was used for the release of 1-MCP, where about 25 mg of S1 and S4, containing 1-MCP, was heated to 50° C. Headspace samples were withdrawn periodically to quantify the released 1-MCP. Results showed that 1-MCP released completely from AS1 within 90 minutes, however, only about 6% released from ES4 after 360 minutes (6 hours; Table 5).

Thus, the energy required to release 1-MCP from samples S1 and S4 are very different, and therefore the means of holding 1-MCP in S1 and S4 (e.g., adsorption vs. encapsulation) are also different. A lower amount of energy is sufficient to release 1-MCP from AS1, which may be due to easy movement of energy through the S1 MCPN structure, while the S4 molecular encapsulation structure includes a cage structure that causes higher levels of energy to be required to both enter the structure and also overcome the weak attractive forces to release 1-MCP.

TABLE 5

Release of 1-MCP from AS1 and ES4 at 50° C.

| AS1 at 50° C. | | ES4 at 50° C. | |
|---|---|---|---|
| Time (min) | % Released | Time (min) | % Released |
| 5 | 31.3 | 5 | 1.3 |
| 15 | 73.2 | 15 | 1.7 |
| 35 | 85.1 | 35 | 2.4 |

TABLE 5-continued

Release of 1-MCP from AS1 and ES4 at 50° C.

| AS1 at 50° C. | | ES4 at 50° C. | |
|---|---|---|---|
| Time (min) | % Released | Time (min) | % Released |
| 50 | 94.0 | 50 | 2.9 |
| 65 | 100.0 | 65 | 3.3 |
| 80 | 100.0 | 95 | 3.4 |
|  |  | 120 | 4.2 |
|  |  | 165 | 4.2 |
|  |  | 210 | 5.0 |
|  |  | 360 | 6.2 |

Figure 4:
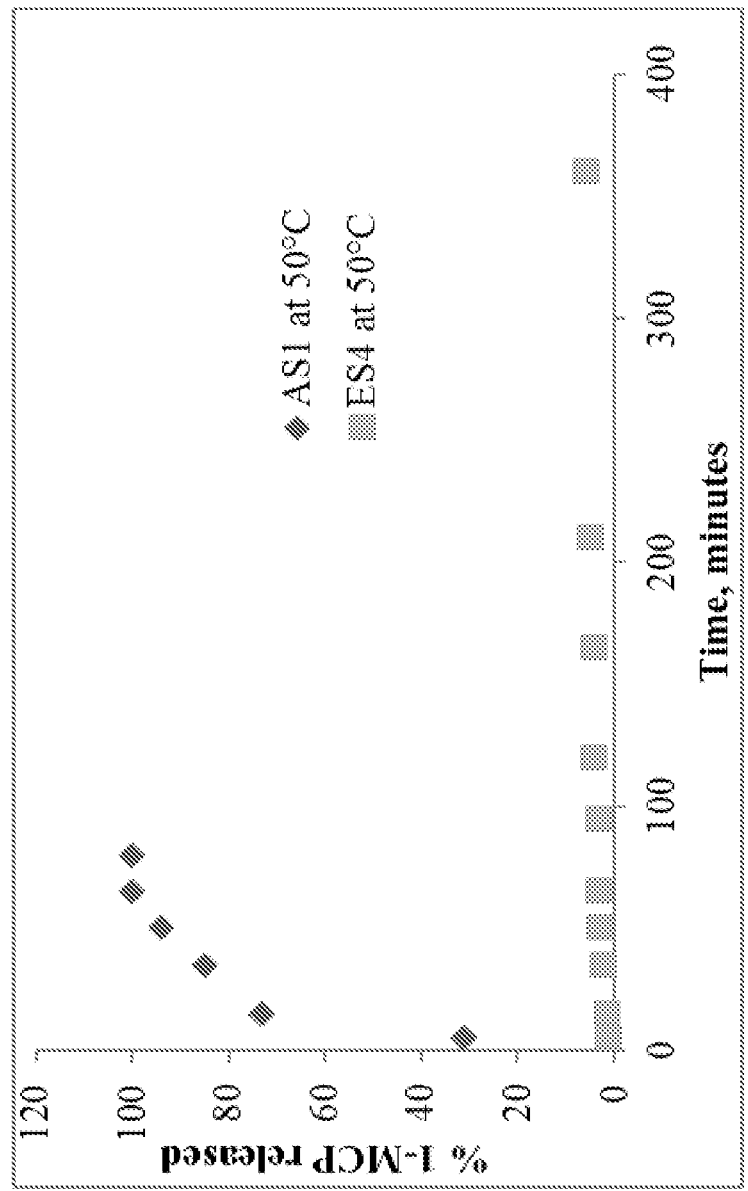
FIG. 4 is a graph illustrating the release of 1-MCP from the encapsulant and the absorbent complexes by heating at 50° C., and shows data corresponding to Table 5, in accordance with various embodiments.

FIG. 4 is a graph illustrating the release of 1-MCP from the encapsulant and the absorbent complexes by heating at 50° C., and shows data corresponding to Table 5, in accordance with various embodiments. As shown in FIG. 4, at 50° C., 1-MCP released completely from AS1 within 90 minutes, however, only around 6% released from ES4 after 360 minutes (6 hours).

Example 10: Recyclability of the S1 Adsorbent

This Example demonstrates the recyclability of the S1 adsorbent in releasing and readsorbing 1-MCP. This recyclability was evaluated by releasing 1-MCP from the adsorbed S1 sample and reusing the adsorbent for subsequent adsorption. Once 1-MCP was released completely from the S1 adsorption, using methods C and E, the resultant adsorbent was separated and used for adsorption again. When method C was used for releasing 1-MCP, the resultant adsorbent was removed after complete release, cooled and vacuum dried overnight. Then, 25 mg of the dried adsorbent was reused for adsorption of 1-MCP using method A. The S1 sample was able to be recycled, and about 2.5% of adsorption level was achieved with the recycling process.

When method E was used for releasing 1-MCP, the resultant adsorbent was removed after complete release by centrifugation process and kept in a vacuum oven overnight to remove water. Then, 25 mg of the dried adsorbent was adsorbed using method A. The S1 sample was able to be recycled, and about 1.01% of adsorption level was achieved with the recycling process.

Example 11: TEM Analysis of MCPN Before and After Adsorption of 1-MCP

Figure 5B:
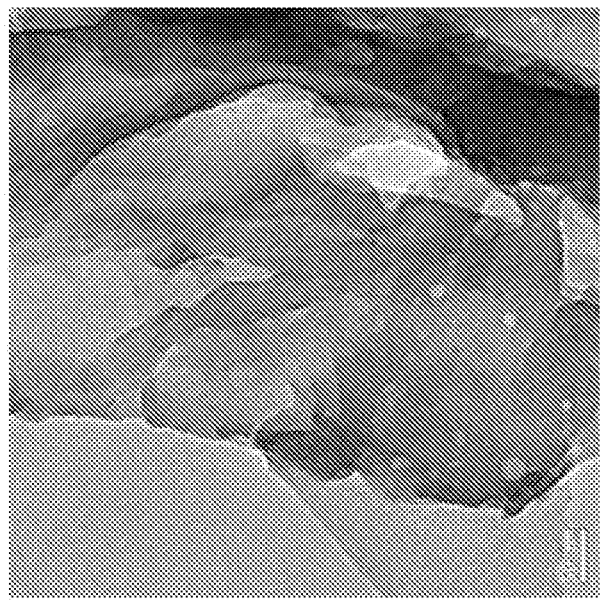
FIGS. 5A and 5B are two digital images showing TEM analyses of MCPN before and after complex formation with 1-MCP; in accordance with various embodiments.
Figure 5A:
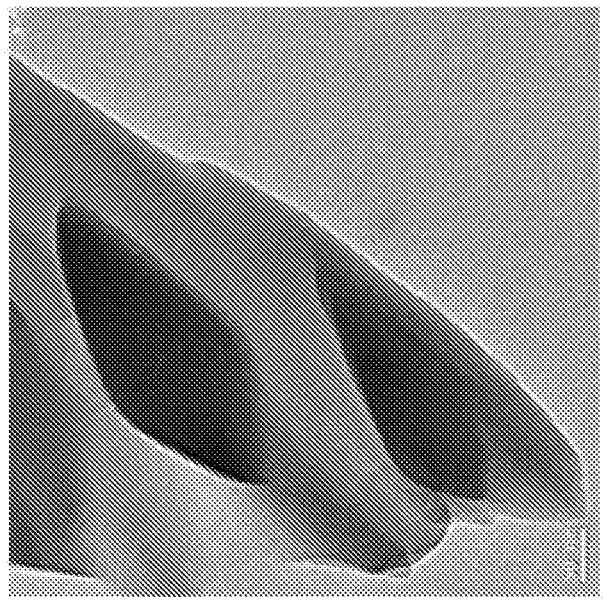

This Example illustrates the structural changes in an MCPN upon adsorption of 1-MCP. Tunneling electron microscopy (TEM) analyses were conducted to visualize the structure before and after adsorption of 1-MCP. FIGS. 5A and 5B are two digital images showing TEM analyses of MCPN before and after complex formation with 1-MCP; in accordance with various embodiments.

As shown in FIG. 5A, the surface of control sample (before adsorption) is smooth, while after adsorption (FIG. 5B), the surface becomes rough because of the attachment of 1-MCP molecules.

Example 12: Bioassay Studies

This Example demonstrates that 1-MCP released from a MCPN-1-MCP complex exerts the expected biological effects on plant materials. Bioassay studies were carried out by releasing from the invention complex 1000 ppb of 1-MCP (volume/volume) in the headspace of a 265 airtight Pyrex Glass Treatment Chamber containing 50 partially ripened tomatoes (approximately 50% green and 50% red). The airtight lid of the chamber was opened 16 hours after 1-MCP release was triggered from a MCPN-1-MCP complex. Release was triggered with water, and after the lid was opened, the internal atmosphere of the chamber to was allowed to equilibrate to normal ambient air levels of $O_2$ and $CO_2$. A separate batch of 50 tomatoes that were not exposed to 1-MCP served as a control. Both treated and non-treated fruits were held at 22° C. for shelf life evaluation. The control fruit had a shelf life of 7 days, while the fruit treated with 1-MCP released from the MCPN-1-MCP complex had a shelf life of 14 days at 22° C.

Example 13: Testing of Commercially Available MCPNs

This Example illustrates the efficacy of several commercially available MCPNs at adsorbing 1-MCP. Commercially available MCPNs were tested along with lab-made MCPNs for their ability to adsorb. The MCPNs included Calcium 4,4'-sulfonyldibenzoic acid (MCPN-a), magnesium formate (MCPN-b), aluminum terephthalate (MCPN-c), copper benzene-1,3,5-tricarboxylate (MCPN-d), iron 1,3,5-benzenetricarboxylate, (MCPN-e), cobalt formate (MCPN-f), manganese formate (MCPN-g), nickel formate (MCPN-h), and 2-methylimidazole zinc salt (MCPN-i). 1-MCP adsorption was carried out using a two-jar setup substantially as described above. 1-MCP was generated in one jar and the adsorption took place in another one. Before the initiation of the adsorption process, about 1 g of MCPN was activated in a vacuum oven at 100° C. for at least 8 hours to remove moisture or solvents. MCPN was placed with desiccants in the adsorption jar in which vacuum was created by a vacuum pump.

In the other jar, lithium salt was mixed with water to generate 1-MCP (headspace concentration>0.1 atm or 100,000 ppm). The two jars (1-MCP generation jar and the adsorption jar) were then connected to introduce 1-MCP into the adsorption jar. The adsorption continued for 20 hours.

Quantification of the adsorbed 1-MCP was accomplished by mixing the resultant MCPN powder in water in an airtight jar. The 1-MCP released in headspace was measured after 1 hour based on the method described by Mir et al., "Harvest Maturity, Storage Temperature and 1-MCP Application Frequency Alter Firmness Retention and Chlorophyll Fluorescence of "Redchief Delicious" Apples," *Journal of American society of horticultural science,* 2001, 126(5): 618-624).

Table 6 demonstrates the adsorption ratio of 1-MCP by different MCPNs ranging from 0.1% to 8.8%. MCPN-b showed the highest adsorption, followed by MCPN-h, MCPN-g, and MCPN-f, which were approximately the same level as MCPN-b at 7-9%, and MCPN-a had lower adsorption ratio at 2.3%. Other MCPNs, including MCPN-c, MCPN-d, MCPN-e, and MCPN-i had almost no adsorption.

TABLE 6

Adsorption of 1-MCP into MCPNs

|  | MCPN-a | MCPN-b | MCPN-c | MCPN-d | MCPN-e | MCPN-f | MCPN-g | MCPN-h | MCPN-i |
|---|---|---|---|---|---|---|---|---|---|
| Adsorption ratio (%) | 2.3 | 8.8 | 0.3 | 0.3 | 0.2 | 7.5 | 8.1 | 8.5 | 0.1 |

Example 14: Evaluation of the Adsorption-Desorption Properties of MCPN

This Example illustrates the adsorption-desorption properties of an MCPN. To evaluate the adsorption-desorption properties of MCPN at 1 atm, isobutene was used as a marker to simulate 1-MCP at 1 atm due to its structural similarity to 1-MCP and similar molecular weight. Quantification was conducted using an automated micro-pore gas analyzer, Autosorb-1 MP (Quantachrome Instruments). The adsorption analysis was conducted under 1 atm isobutene, and desorption was conducted under 1 atm air. Alpha cyclodextrin (C-a) and beta cyclodextrin (C-b) were used as control for comparison purpose.

Table 7 illustrates that MCPN-b had the highest isobutene uptake of 140 mg/g followed by MCPN-f 105 mg/g and MCPN-a 63 mg/g, while there was no uptake by C-a and C-b. The rate of adsorption for MCPN-b and MCPN-f was instant which was much faster than MCPN-a, which was almost 10 hours for maximum adsorption. The complete desorption for MCPN-b and MCPN-f occurred within 3 hours, and the final uptake after reaching desorption plateau was low at almost zero. However, the desorption for MCPN-a was much slower and was expected to plateau at a relatively higher uptake level after 10 hours.

TABLE 7

Adsorption-desorption property of MCPN's for isobutene

|  | MCPN-a | MCPN-b | MCPN-f | C-a | C-b |
|---|---|---|---|---|---|
| Isobutene uptake (mg/g) | 63 | 140 | 105 | 0 | 0 |
| Adsorption time (hr) | 10 | Instant | Instant | NA | NA |
| Desorption time (hr) | 10+ | 3 | 3 | NA | NA |

Example 15: Stability and Recyclability of MCPN-a in Water

This Example illustrates the stability and recyclability of MCPN-a in water. X-ray analysis was carried out to determine the structural change in MCPN-a before and after hydrolysis. C-a was also analyzed for comparison purposes. Approximately 2 mg of MCPN-a was first soaked separately in 2 ml of water for 1 hour, 5 hours, and 20 hours and then dried at 120° C. and filtered to be recycled. Powder X-ray diffraction patterns were recorded on a Rigaku D/M-2200T automated diffractometer (Ultima+) using Cu Kα radiation ($\lambda=1.5406$ Å). A graphite monochromator was used and the generator power settings were 44 kV and 40 mA. Data was collected between a 2 theta of 3-50° C. at a scanning speed of 3.0° C./min.

Figure 6A:
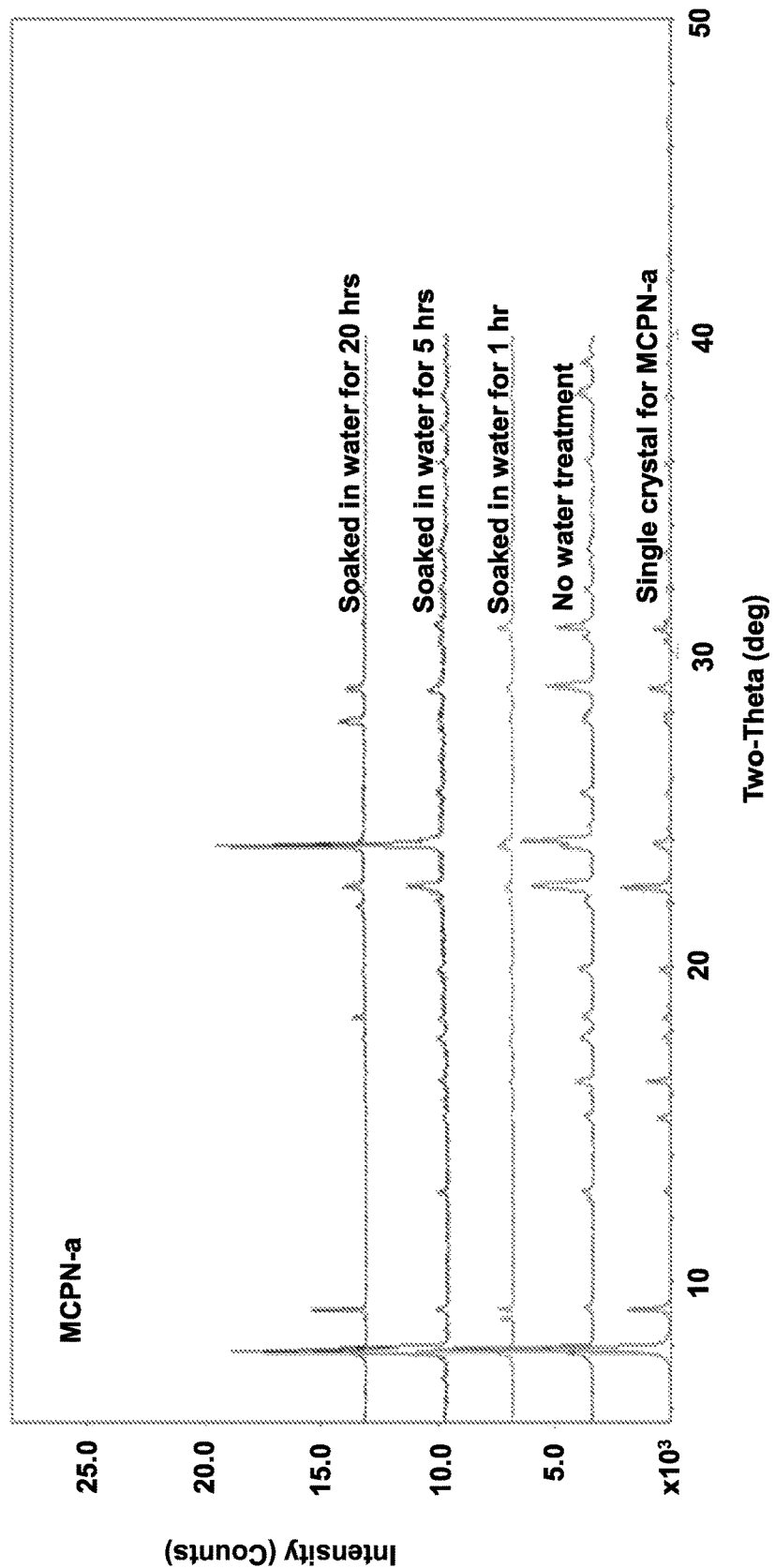
FIGS. 6A and 6B illustrate X-ray diffraction patterns of MCPN before (FIG. 6A) and after (FIG. 6B) dissolution in water, in accordance with various embodiments.
Figure 6B:
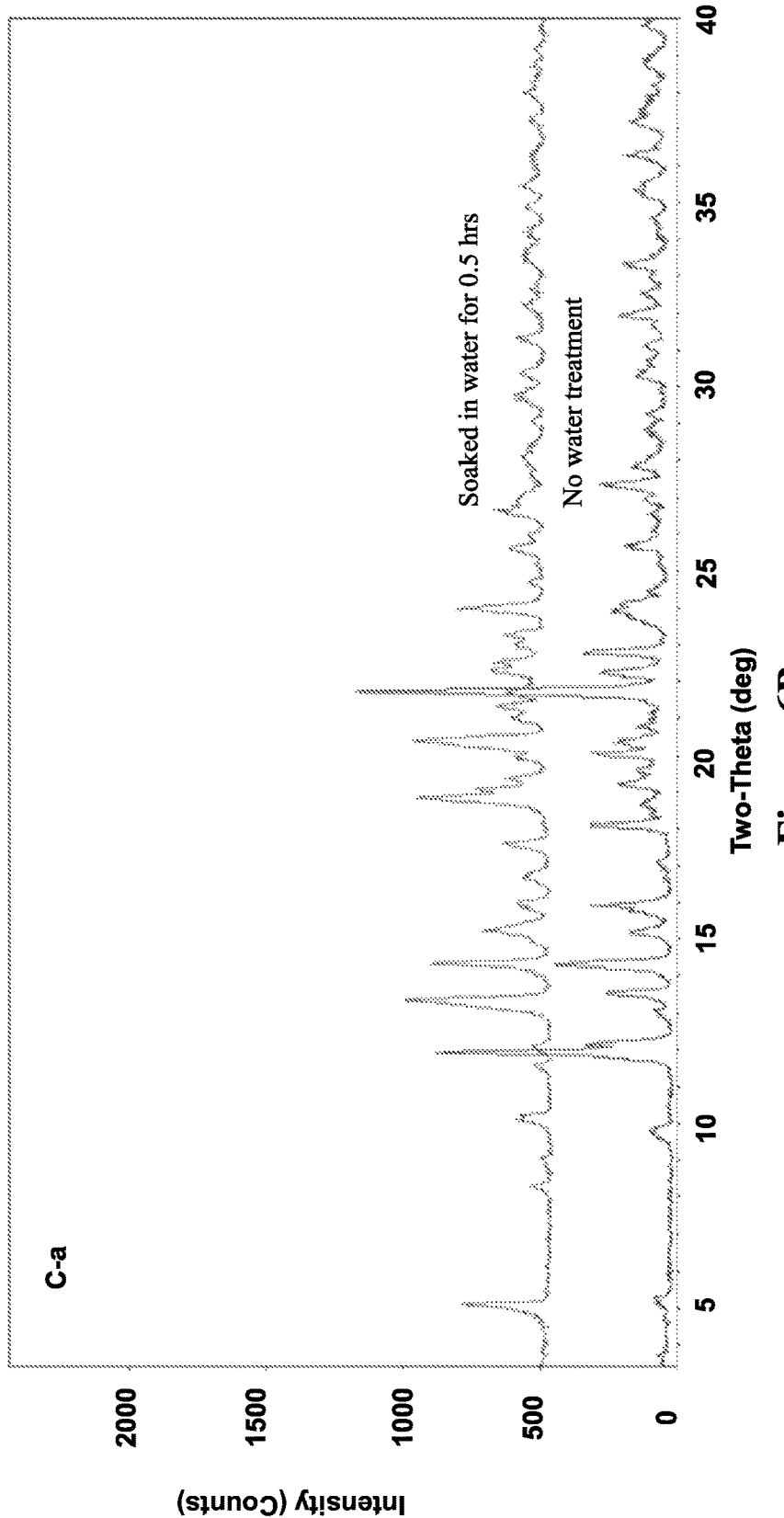

FIGS. 6A and 6B illustrate X-ray diffraction patterns of MCPN before (FIG. 6A) and after (FIG. 6B) dissolution in water, in accordance with various embodiments. The X-ray pattern of MCPN-a did not change after water treatment up to 20 hours, indicating that it is stable and recyclable in water. However, C-a had a dramatic structure change after 1 hour soaking in water. The results indicate another advantage of using MCPN-a as an adsorbent for 1-MCP as compared to C-a as a 1-MCP encapsulant because of its stability and recyclability in water.

Example 16: Thermal Stability of MCPN

This Example illustrates the thermal stability of MCPN. Thermogravimetric analysis (TGA) was conducted to determine the temperature that causes structural change in MCPN. MCPN-f and MCPN-b were analyzed and C-a and C-b were used as controls. TGA data was collected on a TA Q5000 Analyzer with a temperature ramping rate of 10° C./min from room temperature to 600° C. under nitrogen gas flow.

Table 8 illustrates that the decomposing temperature of MCPN-b was 400° C., which was higher than the decomposing temperature of 275° C. for MCPN-f, which was similar to C-a and C-b. Thus, MCPN-b may be recycled as a 1-MCP adsorbent, even after heat treatment.

TABLE 8

Decomposing temperature of MCPNs

|  | MCPN-f | MCPN-b | C-a | C-b |
|---|---|---|---|---|
| Temperature (° C.) | 275 | 400 | 280 | 280 |

Example 17: Stability of Active Ingredient Formulation (AIF) in Capsules and Tablets This Example demonstrates the stability of AIF in three types of capsules: capsules filled with MCPN-b/AIF complex and glycerol (MCPN-G), capsules filled with MCPN-b/AIF with liquid formulation (MCPN-LF), and capsules filled with starch and mineral oil (MCPN-SOL). To make MCPN-G, the capsules were first filled with MCPN-B/AIF, and approximately 0.6 mL of glycerol was added. To make MCPN-LF, a liquid formulation (blend of 78% glycerol/9% hydroxypropyl cellulose/13% polysorbate) and MCPN-b/AIF was mixed using a vortex mixer for 10 minutes. Approximately 0.5 mL of the mixture was dispensed into each capsule. To make MCPN-SOL, 1.5 g of starch and 0.06 g of MCPN were added to each capsule, and then mineral oil was added to the capsule. The particle size of MCPN in MCPN-LF was less than 0.21 mm. The range of particle size of other formulations was from approximately 0.21 mm to 1.5 mm.

The stability of AIF in three tablets was evaluated. MCPN-T1 was made using food grade modified starch as the filler. The composition of a MCPN-T1 was 1.2 g with 0.5% 1-MCP. Excess pressure was used to compress the ingredients into MCPN-T1 tablets. Two materials were tested for MCPN-B1 (1) MCPN-B1a (20% PVOH solution)

and (2) MCPN-B1b (50% gelatin solution). Approximately 1 g of coating material was used for MCPN-B1a and MCPN-B1b. After coating, MCPN-B1a and MCPN-B1b were dried for approximately 4 hours. The range of particle size of the formulations was from approximately 0.21 mm to 1.5 mm. For comparison purposes, powder formulation without any barrier protection (MCPN-P1) was also tested.

Table 9 illustrates the retention of AIF in different formulations. The release from MCPN-P1 was instant, and reached saturation within 1 hour after placing it into a closed chamber, and 79% should be the saturation percentage in 250 mL at given AIF concentration. MCPN-T1 improved the stability and 87% retention was achieved after 9 days. MCPN-B1 further improved the stability. MCPN-B1a and MCPN-B1b improved the retention to 94% and 97% after 9 days, respectively. The higher retention of MCPN-B1b was due to the lower permeability of AIF than MCPN-B1a. MCPN-LF and MCPN-SOL had the best retention. MCPN-G achieved more than 99% retention after 9 days and MCPN-LF and MCPN-SOL had no loss. The slight loss of 1-MCP in MCPN-G on day 4 and onwards was due to glycerol dissolving the gel capsule leading to 1-MCP loss. Glycerol by itself is impermeable to 1-MCP.

TABLE 9

Stability improvement of AIF in MCPN

% Retention of AIF in different treatments

| Time (Day) | MCPN-P1 | MCPN-T1 | MCPN-B1a | MCPN-B1b | MCPN-G | MCPN-LF | MCPN-SOL |
|---|---|---|---|---|---|---|---|
| 1 | 79.08 | 90.05 | 95.12 | 98.55 | 100.00 | 100.00* | 100.00 |
| 2 | 79.05 | 90.39 | 95.11 | 98.06 | 100.00 | 100.00 | 100.00 |
| 3 | | 89.25 | 95.00 | 98.00 | 100.00 | 100.00 | 100.00 |
| 4 | | 89.15 | 95.00 | 98.00 | 99.50 | 100.00 | 100.00 |
| 5 | | 88.24 | 94.9 | 97.88 | 99.30 | 100.00 | 100.00 |
| 6 | | 88.34 | 94.9 | 97.86 | 99.27 | 100.00 | 100.00 |
| 7 | | 88.29 | 94.87 | 97.82 | 99.21 | 100.00 | 100.00 |
| 8 | | 87.40 | 94.86 | 97.81 | 99.18 | 100.00 | 100.00 |
| 9 | | 87.22 | 94.86 | 97.81 | 99.14 | 100.00 | 100.00 |

*Determined by the detection limit of the method for AIF (10 ppb)

Example 18: Uniformity of MCPN-LF

This Example illustrates the uniformity of MCPN-LF. After mixing MCPN-B/AIF and dispersing agent (blend of 78% glycerol/9% hydroxypropyl cellulose/13% polysorbate), five small portions with known amounts of the mixture were dissolved into water in individual closed jars to release AIF. The particle size of MCPN in MCPN-LF was less than 0.21 mm. Table 10 illustrates that the five portions were uniform with minimum variation. The percentage of AIF in liquid formulation was between 0.194 and 0.198.

TABLE 10

Uniformity of AIF in MCPN-LF

| Capsule # | Amount of liquid formulation (g) | AIF (ppm) in headspace of the closed jar | AIF (mg) in liquid formulation | % of AIF in liquid formulation |
|---|---|---|---|---|
| 1 | 0.307 | 1202.04 | 0.604 | 0.196 |
| 2 | 0.430 | 1688.18 | 0.848 | 0.198 |
| 3 | 0.396 | 1521.16 | 0.382 | 0.194 |
| 4 | 0.415 | 1627.56 | 0.818 | 0.196 |
| 5 | 0.366 | 1445.46 | 0.726 | 0.198 |

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method, comprising: contacting an adsorption complex adsorption complex comprising i) 1-methyl cyclopropane (1-MCP) and ii) a metal coordination polymer network (MCPN) comprising a metal node selected from Mg, Mn, Ca, Cu, Al, Zn, Fe, or a combination thereof, and one or more ligands coupled to the metal node with an aqueous fluid, wherein the 1-MCP is adsorbed to a surface of the MCPN.

2. The method of claim 1, wherein contacting comprises contacting the adsorption complex with an aqueous fluid produced via transpirational moisture evolution from packaged plants or plant parts.

3. The method of claim 1, wherein the adsorption complex is contained within a 1-MCP-MCPN complex container.

4. The method of claim 1, wherein the surface of the MCPN is a surface defining a pore in the MCPN.

5. The method of claim 1, wherein the surface of the MCPN is a surface outside of a pore in the MCPN.

6. The method of claim 1, wherein the metal node is Mg.

7. The method of claim 1, wherein the metal node is Mn.

8. The method of claim 1, wherein the metal node is Ca.

9. The method of claim 1, wherein the metal node is Cu.

10. The method of claim 1, wherein the metal node is Al.

11. The method of claim 1, wherein the metal node is Zn.

12. The method of claim 1, wherein the metal node is Fe.

13. The method of claim 6, wherein the surface of the MCPN is a surface defining a pore in the MCPN.

14. The method of claim 6, wherein the surface of the MCPN is a surface outside of a pore in the MCPN.

15. The method of claim 1, wherein the contacting is used to inhibit an ethylene response in a plant or plant parts.

16. The method of claim 1, wherein the contacting is used to inhibit an ethylene response in a plant or plant parts.

17. The method of claim 16, wherein the inhibition of ethylene response results in a modification in the plant or plant parts selected from the group consisting of germination, flower and leaf senescence, fruit ripening, leaf abscission, root nodulation, programmed cell death, and responsiveness to stress and pathogen attack.

18. The method of claim 16, wherein the inhibition of ethylene response results in an inhibition, reduction, or slowing of fruit ripening.

19. The method of claim 16, wherein the inhibition of ethylene response results in inhibiting internal concentration of naturally produced ethylene from increasing to about 0.1-1.0 (ppm).

* * * * *